(12) United States Patent
Sarwal

(10) Patent No.: US 10,317,401 B2
(45) Date of Patent: Jun. 11, 2019

(54) METHODS AND COMPOSITIONS FOR THE PREDICTION AND TREATMENT OF FOCAL SEGMENTAL GLOMERULOSCLEROSIS

(71) Applicant: Minnie Sarwal, Portola Valley, CA (US)

(72) Inventor: Minnie Sarwal, Portola Valley, CA (US)

( * ) Notice: Subject to any disclaimer, the term of this patent is extended or adjusted under 35 U.S.C. 154(b) by 0 days.

(21) Appl. No.: 15/301,672

(22) PCT Filed: Apr. 3, 2015

(86) PCT No.: PCT/US2015/024388
§ 371 (c)(1),
(2) Date: Oct. 3, 2016

(87) PCT Pub. No.: WO2015/154056
PCT Pub. Date: Oct. 8, 2015

(65) Prior Publication Data
US 2017/0176434 A1      Jun. 22, 2017

Related U.S. Application Data

(60) Provisional application No. 61/975,692, filed on Apr. 4, 2014.

(51) Int. Cl.
*G01N 33/564* (2006.01)
*C07K 16/28* (2006.01)

(52) U.S. Cl.
CPC ....... *G01N 33/564* (2013.01); *C07K 16/2878* (2013.01); *C07K 2317/21* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 2003/0103976 A1* | 6/2003 | Serizawa | C07K 14/70575 424/146.1 |
| 2010/0015139 A1* | 1/2010 | Bansal | C07K 16/40 424/133.1 |
| 2013/0236495 A1 | 9/2013 | Wagner | |
| 2013/0266605 A1 | 10/2013 | Watt et al. | |
| 2014/0093497 A1 | 4/2014 | Reimann et al. | |
| 2015/0132302 A1* | 5/2015 | Alexander | A61K 39/0008 424/134.1 |

OTHER PUBLICATIONS

Harlow et al. (Antibodies a laboratory manual. Cold Spring Harbor, New York: Cold Spring Harbor Laboratory Press, 1989. pp. 141-156). (Year: 1989).*
Davenport et al. (J. Clinical Apheresis 2001 vol. 16, p. 175-178). (Year: 2001).*
Sakai, K. et al. (2010). "Protocol Biopsies for Focal Segmental Glomerulosclerosis Treated With Plasma Exchange and Rituximab in a Renal Transplant Patient," *Clin Transplant* 24(Suppl. 22):60-65.
Sarwal, M. et al. (Apr. 26, 2013). "A Pivotal Circulating Antibody Panel for Pre-Transplant Prediction of FSGS Recurrence After Kidney Transplantation," *Am J Transplant*. 13(Suppl. 5):123, Abstract No. 298, one page.
International Preliminary Report on Patentability and Written Opinion dated Oct. 13, 2016, for PCT/US2015/024388, filed on Apr. 3, 2015, 10 pages.
International Search Report and Written Opinion of the International Searching Authority dated Jul. 6, 2015 for PCT Application No. PCT/US2015/024388, filed on Apr. 3, 2015, 13 pages.

* cited by examiner

*Primary Examiner* — Changhwa J Cheu
(74) *Attorney, Agent, or Firm* — Morrison & Foerster LLP

(57) ABSTRACT

Provided herein are methods and compositions for the prediction and treatment of focal segmental glomerulosclerosis and other proteinuric renal diseases such as native FSGS, minimal change disease, glomerular nephritis, membrano-proliferative glomerular nephritis (membranous), or IgA glomerular nephritis (membranous).

5 Claims, 24 Drawing Sheets

Specification includes a Sequence Listing.

Increased Immunogenecity of
β-strands of CD40 on FSGS $p < 0.002$

Average Log2 [RFU]

Ctrl         rFSGS

SEQUENCE LISTING

```
<160> NUMBER OF SEQ ID NOS: 69

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Ser Gln Cys Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Glu Ser Glu Phe
1

<210> SEQ ID NO 3
<211> LENGTH: 15
```

```
<212> TYPE: PRT
<213> ORGANISM: Artificial Sequence
<220> FEATURE:
<223> OTHER INFORMATION: Synthetic Construct

<400> SEQUENCE: 3

Met Val Arg Leu Pro Leu Gln Cys Val Leu Trp Gly Cys Leu Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Pro Leu Gln Cys Val Leu Trp Gly Cys Leu Leu Thr Ala Val His
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Val Leu Trp Gly Cys Leu Leu Thr Ala Val His Pro Glu Pro Pro
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Cys Leu Leu Thr Ala Val His Pro Glu Pro Pro Thr Ala Cys Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Ala Val His Pro Glu Pro Pro Thr Ala Cys Arg Glu Lys Gln Tyr
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Glu Pro Pro Thr Ala Cys Arg Glu Lys Gln Tyr Leu Ile Asn Ser
1               5                   10                  15

<210> SEQ ID NO 9
<211> LENGTH: 15
<212> TYPE: PRT
```

```
<213> ORGANISM: Artificial Sequence
<220> FEATURE:
<223> OTHER INFORMATION: Synthetic Construct

<400> SEQUENCE: 9

Ala Cys Arg Glu Lys Gln Tyr Leu Ile Asn Ser Gln Cys Cys Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Lys Gln Tyr Leu Ile Asn Ser Gln Cys Cys Ser Leu Cys Gln Pro
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Ile Asn Ser Gln Cys Cys Ser Leu Cys Gln Pro Gly Gln Lys Leu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Cys Cys Ser Leu Cys Gln Pro Gly Gln Lys Leu Val Ser Asp Cys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Cys Gln Pro Gly Gln Lys Leu Val Ser Asp Cys Thr Glu Phe Thr
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Gln Lys Leu Val Ser Asp Cys Thr Glu Phe Thr Glu Thr Glu Cys
1               5                   10                  15

<210> SEQ ID NO 15
<211> LENGTH: 15
<212> TYPE: PRT
<213> ORGANISM: Artificial Sequence
```

-continued

```
<220> FEATURE:
<223> OTHER INFORMATION: Synthetic Construct

<400> SEQUENCE: 15

Ser Asp Cys Thr Glu Phe Thr Glu Thr Glu Cys Leu Pro Cys Gly
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Glu Phe Thr Glu Thr Glu Cys Leu Pro Cys Gly Glu Ser Glu Phe
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct

<400> SEQUENCE: 17

Thr Glu Cys Leu Pro Cys Gly Glu Ser Glu Phe Leu Asp Thr Trp
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

Pro Cys Gly Glu Ser Glu Phe Leu Asp Thr Trp Asn Arg Glu Thr
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Ser Glu Phe Leu Asp Thr Trp Asn Arg Glu Thr His Cys His Gln
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Asp Thr Trp Asn Arg Glu Thr His Cys His Gln His Lys Tyr Cys
 1               5                  10                  15

<210> SEQ ID NO 21
<211> LENGTH: 15
<212> TYPE: PRT
<213> ORGANISM: Artificial Sequence
<220> FEATURE:
```

<223> OTHER INFORMATION: Synthetic Construct

<400> SEQUENCE: 21

Arg Glu Thr His Cys His Gln His Lys Tyr Cys Asp Pro Asn Leu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Cys His Gln His Lys Tyr Cys Asp Pro Asn Leu Gly Leu Arg Val
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Construct

<400> SEQUENCE: 23

Lys Tyr Cys Asp Pro Asn Leu Gly Leu Arg Val Gln Gln Lys Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Pro Asn Leu Gly Leu Arg Val Gln Gln Lys Gly Thr Ser Glu Thr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic Construct

<400> SEQUENCE: 25

Leu Arg Val Gln Gln Lys Gly Thr Ser Glu Thr Asp Thr Ile Cys
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Gln Lys Gly Thr Ser Glu Thr Asp Thr Ile Cys Thr Cys Glu Glu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Ser Glu Thr Asp Thr Ile Cys Thr Cys Glu Glu Gly Trp His Cys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Thr Ile Cys Thr Cys Glu Glu Gly Trp His Cys Thr Ser Glu Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct

<400> SEQUENCE: 29

Cys Glu Glu Gly Trp His Cys Thr Ser Glu Ala Cys Glu Ser Cys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp His Cys Thr Ser Glu Ala Cys Glu Ser Cys Val Leu His Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Construct

<400> SEQUENCE: 31

Ser Glu Ala Cys Glu Ser Cys Val Leu His Arg Ser Cys Ser Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Construct

<400> SEQUENCE: 32

Glu Ser Cys Val Leu His Arg Ser Cys Ser Pro Gly Phe Gly Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Construct

<400> SEQUENCE: 33

Leu His Arg Ser Cys Ser Pro Gly Phe Gly Val Lys Gln Ile Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Construct

<400> SEQUENCE: 34

Cys Ser Pro Gly Phe Gly Val Lys Gln Ile Ala Thr Gly Val Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic Construct

<400> SEQUENCE: 35

Phe Gly Val Lys Gln Ile Ala Thr Gly Val Ser Asp Thr Ile Cys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic Construct

<400> SEQUENCE: 36

Gln Ile Ala Thr Gly Val Ser Asp Thr Ile Cys Glu Pro Cys Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Construct

<400> SEQUENCE: 37

Gly Val Ser Asp Thr Ile Cys Glu Pro Cys Pro Val Gly Phe Phe
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

Thr Ile Cys Glu Pro Cys Pro Val Gly Phe Phe Ser Asn Val Ser
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

```
Pro Cys Pro Val Gly Phe Phe Ser Asn Val Ser Ser Ala Phe Glu
1               5                   10                  15
```

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

```
Gly Phe Phe Ser Asn Val Ser Ser Ala Phe Glu Lys Cys His Pro
1               5                   10                  15
```

<210> SEQ ID NO 41
<211> LENGTH: 15
<212> TYPE: PRT
<213> ORGANISM: Artificial Sequence
<220> FEATURE:
<223> OTHER INFORMATION: Synthetic Construct

<400> SEQUENCE: 41

```
Asn Val Ser Ser Ala Phe Glu Lys Cys His Pro Trp Thr Ser Cys
1               5                   10                  15
```

<210> SEQ ID NO 42
<211> LENGTH: 15
<212> TYPE: PRT
<213> ORGANISM: Artificial Sequence
<220> FEATURE:
<223> OTHER INFORMATION: Synthetic Construct

<400> SEQUENCE: 42

```
Ala Phe Glu Lys Cys His Pro Trp Thr Ser Cys Glu Thr Lys Asp
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43

```
Cys His Pro Trp Thr Ser Cys Glu Thr Lys Asp Leu Val Val Gln
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

```
Thr Ser Cys Glu Thr Lys Asp Leu Val Val Gln Gln Ala Gly Thr
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Synthetic Construct

<400> SEQUENCE: 45

Thr Lys Asp Leu Val Val Gln Gln Ala Gly Thr Asn Lys Thr Asp
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic Construct

<400> SEQUENCE: 46

Val Val Gln Gln Ala Gly Thr Asn Lys Thr Asp Val Val Cys Gly
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47

Ala Gly Thr Asn Lys Thr Asp Val Val Cys Gly Pro Gln Asp Arg
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic Construct

<400> SEQUENCE: 48

Lys Thr Asp Val Val Cys Gly Pro Gln Asp Arg Leu Arg Ala Leu
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic Construct

<400> SEQUENCE: 49

Val Cys Gly Pro Gln Asp Arg Leu Arg Ala Leu Val Val Ile Pro
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Gln Asp Arg Leu Arg Ala Leu Val Val Ile Pro Ile Ile Phe Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Arg Ala Leu Val Val Ile Pro Ile Ile Phe Gly Ile Leu Phe Ala

-continued

<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Val Ile Pro Ile Ile Phe Gly Ile Leu Phe Ala Ile Leu Leu Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct

<400> SEQUENCE: 53

Ile Phe Gly Ile Leu Phe Ala Ile Leu Leu Val Leu Val Phe Ile
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic Construct

<400> SEQUENCE: 54

Leu Phe Ala Ile Leu Leu Val Leu Val Phe Ile Lys Lys Val Ala
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Construct

<400> SEQUENCE: 55

Leu Leu Val Leu Val Phe Ile Lys Lys Val Ala Lys Lys Pro Thr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Val Phe Ile Lys Lys Val Ala Lys Lys Pro Thr Asn Lys Ala Pro
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic Construct

<400> SEQUENCE: 57

Lys Val Ala Lys Lys Pro Thr Asn Lys Ala Pro His Pro Lys Gln
1               5                   10                  15

-continued

<210> SEQ ID NO 58
<211> LENGTH: 15
<212> TYPE: PRT
<213> ORGANISM: Artificial Sequence
<220> FEATURE:
<223> OTHER INFORMATION: Synthetic Construct

<400> SEQUENCE: 58

Lys Pro Thr Asn Lys Ala Pro His Pro Lys Gln Glu Pro Gln Glu
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic Construct

<400> SEQUENCE: 59

Lys Ala Pro His Pro Lys Gln Glu Pro Gln Glu Ile Asn Phe Pro
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

Pro Lys Gln Glu Pro Gln Glu Ile Asn Phe Pro Asp Asp Leu Pro
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

Pro Gln Glu Ile Asn Phe Pro Asp Asp Leu Pro Gly Ser Asn Thr
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Asn Phe Pro Asp Asp Leu Pro Gly Ser Asn Thr Ala Ala Pro Val
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

Asp Leu Pro Gly Ser Asn Thr Ala Ala Pro Val Gln Glu Thr Leu
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic Construct

<400> SEQUENCE: 64

Ser Asn Thr Ala Ala Pro Val Gln Glu Thr Leu His Gly Gln Gln
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic Construct

<400> SEQUENCE: 65

Ala Pro Val Gln Glu Thr Leu His Gly Cys Gln Pro Val Thr Gln
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic Construct

<400> SEQUENCE: 66

Glu Thr Leu His Gly Cys Gln Pro Val Thr Gln Glu Asp Gly Lys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic Construct

<400> SEQUENCE: 67

Gly Cys Gln Pro Val Thr Gln Glu Asp Gly Lys Glu Ser Arg Ile
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic Construct

<400> SEQUENCE: 68

Val Thr Gln Glu Asp Gly Lys Glu Ser Arg Ile Ser Val Gln Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic Construct

<400> SEQUENCE: 69

Gln Glu Asp Gly Lys Glu Ser Arg Ile Ser Val Gln Glu Arg Gln
1               5                   10                  15

METHODS AND COMPOSITIONS FOR THE PREDICTION AND TREATMENT OF FOCAL SEGMENTAL GLOMERULOSCLEROSIS

CROSS-REFERENCE TO RELATED APPLICATIONS

This application is a National Phase application under 35 U.S.C. § 371 of International Application No. PCT/US2015/024388, filed on Apr. 3, 2015, which claims priority to U.S. Provisional Application Ser. No. 61/975,692, filed on Apr. 4, 2014, the disclosure of each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735292000100SEQLIST.TXT, date recorded: Jan. 15, 2019, size: 16 KB).

BACKGROUND OF THE INVENTION

Primary Focal Segmental Glomerulosclerosis (FSGS) is a proteinuric glomerular disease that affects podocyte function and survival and results in a typical pattern of histopathological injury including glomerulosclerosis on kidney biopsy [1, 2].

Renal transplant patients with primary FSGS or native FSGS face a high risk of recurrence of FSGS (recurrent FSGS, rFSGS) in the allograft (20 to 40% after a first transplant and up to 80% for re-transplantation) [3, 4]. Recurrence of focal segmental glomerulosclerosis (rFSGS) after kidney transplantation leads to graft loss and has a potentially detrimental course toward the loss of renal function.

Native FSGS (nFSGS) can develop from a variety of causes, including genetic, toxicity, or for example from minimal change disease, a kidney disorder that can lead to nephrotic syndrome, although the nephrons of the kidney look normal under a regular microscope. Native FSGS can also develop from other proteinuric kidney diseases.

Immuneadsorption alleviates renal graft dysfunction in some cases and suggests implication of circulating antibodies as a potential culprit of the disease. Clinical association studies [5, 6] and animal and cell studies have identified elevated pre and post-transplantation serum levels of the soluble urokinase receptor (suPAR) [7, 8] as an altered in native and recurrent FSGS [7]. SuPAR levels, though correlative with FSGS recurrence [7, 8], may be non-specific and have been found elevated in other conditions such as sepsis.

Circulating permeability factors and auto-antibodies (autoantibody), such as anti-actin, anti-ATP synthase, and anti-nephrin [9-11] have been implicated in the pathogenesis of rFSGS. It was suggested that autoantibody participate in the pathogenesis of rFSGS, as autoantibody directed against podocyte tyrosine phosphatase receptor-O, nephrin or anti-Thy1.1[12, 13], when injected in animal models, can cause an increase in glomerular permeability, and rFSGS can be improved in some cases by manipulation of the humoral response by plasmapheresis and rituximab [14-17].

Observations notwithstanding, improvements in pre-transplant risk stratification for rFSGS, nFSGS, minimal change disease, and other proteinuric kidney diseases and subsequent treatment remain a major clinical challenge. The present invention provides compositions and methods for pre-transplant biomarkers of these diseases and appropriate treatment paradigms.

BRIEF SUMMARY OF THE INVENTION

Provided herein are methods, compositions and kits useful for identifying the risk an individual faces of developing recurrent FSGS (rFSGS), native FSGS, minimal change disease, glomerular nephritis, membrano-proliferative glomerular nephritis (membranous), or IgA glomerular nephritis (membranous), for predicting whether an individual will develop rFSGS, native FSGS, minimal change disease, glomerular nephritis, membrano-proliferative glomerular nephritis (membranous), or IgA glomerular nephritis (membranous) as well as for the treatment of rFSGS, native FSGS, minimal change disease, glomerular nephritis, membrano-proliferative glomerular nephritis (membranous), or IgA glomerular nephritis (membranous). This invention will allow for the determination of the risk of FSGS recurrence, native FSGS, minimal change disease, glomerular nephritis, membrano-proliferative glomerular nephritis (membranous), or IgA glomerular nephritis (membranous) in identified high-risk patients and positively impact graft function and survival with future targeted treatments.

In one aspect, the invention provides a method of predicting whether an individual will develop recurrent focal segmental glomerulosclerosis (rFSGS), native FSGS, minimal change disease, glomerular nephritis, membrano-proliferative glomerular nephritis (membranous), or IgA glomerular nephritis (membranous) comprising: contacting a biological sample from the individual with a binding agent; and detecting the binding of the binding agent to at least one autoantibody in the sample, wherein the autoantibody is selected from the autoantibodies listed in Table 2; wherein the binding of the binding agent to the autoantibody in the sample is increased as compared to the binding of the binding agent to a reference standard, whereby the increase in binding indicates the risk of developing rFSGS, native FSGS, minimal change disease, glomerular nephritis, membrano-proliferative glomerular nephritis (membranous), or IgA glomerular nephritis (membranous). In one embodiment the biological sample is serum. In one embodiment the reference standard comprises autoantibody data from individuals who have never suffered from FSGS, non-recurrent FSGS, or rFSGS. In one embodiment, the autoantibody is selected from the group consisting of antibodies to CD40, PTPRO, CGB5, FAS, P2RY11, SNRPB2, APOL2, CCL19, MYLK, and RXRA. In one embodiment, the binding agent is a selected from a CD40 ligand, a PTPRO ligand, a CGB5 ligand, a FAS ligand, a P2RY11 ligand, a SNRPB2 ligand, an APOL2 ligand, a CCL19 ligand, a MYLK ligand, and a RXRA ligand. In one specific embodiment, the autoantibody is an antibody to CD40. In one embodiment, the binding agent binds the autoantibody with a $K_d$ of $10^{-12}$ M to $10^{-5}$ M. In one embodiment, the increase in binding indicates the risk of developing FSGS to at least an 80% degree of accuracy. In one embodiment, the binding agent-autoantibody binding is determined using an ELISA. In one embodiment, the method is carried out after the individual has undergone kidney transplantation. In another embodiment, the method is carried out prior to when the individual has undergone any kidney transplantation. In one specific embodiment, the method is carried out 1 day prior to when the individual undergoes kidney transplantation.

In another aspect, the invention provides a method of predicting whether an individual will develop recurrent focal segmental glomerulosclerosis (rFSGS), native FSGS, minimal change disease, glomerular nephritis, membrano-proliferative glomerular nephritis (membranous), or IgA glomerular nephritis (membranous) comprising: contacting a biological sample from the individual with a CD40 antibody; and detecting the binding of the antibody to a CD40 antigen; wherein the binding of the CD40 antibody to the CD40 antigen in the sample is increased as compared to the binding of the CD40 antibody to a reference standard, whereby the increase in binding indicates the risk of developing rFSGS. In one embodiment, the biological sample is serum. In one embodiment, the CD40 antibody recognizes a particular epitope of CD40. In one embodiment, the CD40 antibody is a monoclonal antibody. In one embodiment, the CD40 antibody recognizes a portion of CD40's beta-strand region. In one embodiment, the CD40 antibody recognizes an epitope represented by a stretch of amino acids comprising ESEF (SEQ ID NO: 2). In one embodiment, the CD40 antibody recognizes an epitope represented by a stretch of amino acids comprising NSQCC (SEQ ID NO: 1). In one embodiment, the reference standard comprises CD40-binding data from individuals who have never suffered from FSGS, non-recurrent FSGS, or rFSGS. In one embodiment, the increase in binding indicates the risk of developing FSGS to at least an 80% degree of accuracy. In one embodiment, the method is carried out after the individual has undergone kidney transplantation. In one embodiment, the method is carried out prior to when the individual has undergone any kidney transplantation. In one embodiment, the method is carried out 1 day prior to when the individual undergoes kidney transplantation.

In another aspect, the invention provides a method of treating an individual who suffers from rFSGS, native FSGS, minimal change disease, glomerular nephritis, membrano-proliferative glomerular nephritis (membranous), or IgA glomerular nephritis (membranous) comprising administering to the individual a blocking factor. In one embodiment, the factor blocks the binding of an autoantibody to a target selected from the group consisting of CD40, PTPRO, CGB5, FAS, P2RY11, SNRPB2, APOL2, CCL19, MYLK, and RXRA. In one embodiment, the target is CD40. In one embodiment, the blocking factor is a blocking antibody. In one embodiment, the target of the blocking antibody is selected from the group consisting of CD40, PTPRO, CGB5, FAS, P2RY11, SNRPB2, APOL2, CCL19, MYLK, and RXRA. In one embodiment, the target is CD40. In one embodiment, the method is carried out after the individual has undergone kidney transplantation. In one embodiment, the method further comprises treating the individual with plasmapheresis. In one embodiment, the method further comprises treating the individual with antibody immuadsorption. In one embodiment, the method further comprises treating the individual with rituximab.

In another aspect, the invention provides a method of preventing an individual from developing rFSGS, native FSGS, minimal change disease, glomerular nephritis, membrano-proliferative glomerular nephritis (membranous), or IgA glomerular nephritis (membranous) comprising administering to the individual a blocking factor. In one embodiment, the factor blocks the binding of an autoantibody to a target selected from the group consisting of CD40, PTPRO, CGB5, FAS, P2RY11, SNRPB2, APOL2, CCL19, MYLK, and RXRA. In one embodiment, the target is CD40. In one embodiment, the blocking factor is a blocking antibody. In one embodiment, the target of the blocking antibody is selected from the group consisting of CD40, PTPRO, CGB5, FAS, P2RY11, SNRPB2, APOL2, CCL19, MYLK, and RXRA. In one embodiment, the target is CD40. In one embodiment, the individual is not suffering from rFSGS at the time of treatment. In one embodiment, the method is carried out after the individual has undergone kidney transplantation. In one embodiment, the method further comprises treating the individual with plasmaphresis. In one embodiment, the method further comprises treating the individual with antibody immuadsorption. In one embodiment, the method further comprises treating the individual with rituximab.

In another aspect, the invention provides an assay kit comprising: reagents for detecting an autoantibody in a biological sample from an individual; a composition comprising a solid surface that contains a binding agent for an autoantibody selected from the group consisting of CD40, PTPRO, CGB5, FAS, P2RY11, SNRPB2, APOL2, CCL19, MYLK, and RXRA; and instructions for use of the assay. In one embodiment, the kit comprises a solid surface containing a binding agent for a CD40 autoantibody. In one embodiment, the binding agent is a selected from a CD40 ligand, a PTPRO ligand, a CGB5 ligand, a FAS ligand, a P2RY11 ligand, a SNRPB2 ligand, an APOL2 ligand, a CCL19 ligand, a MYLK ligand, and a RXRA ligand. In one embodiment, the binding agent is a CD40 ligand.

In another aspect, the invention provides an assay kit comprising: a composition comprising a solid surface that contains a binding agent for a CD40 epitope; reagents for detecting an CD40 epitope in a biological sample from an individual; instructions for use of the assay. In one embodiment, the binding agent is a CD40 antibody. In one embodiment, the CD40 antibody recognizes the epitope represented by a stretch of amino acids comprising ESEF (SEQ ID NO: 2). In one embodiment, the CD40 antibody recognizes the epitope represented by a stretch of amino acids comprising NSQCC (SEQ ID NO: 1).

DETAILED DESCRIPTION OF THE INVENTION

Figure 1:
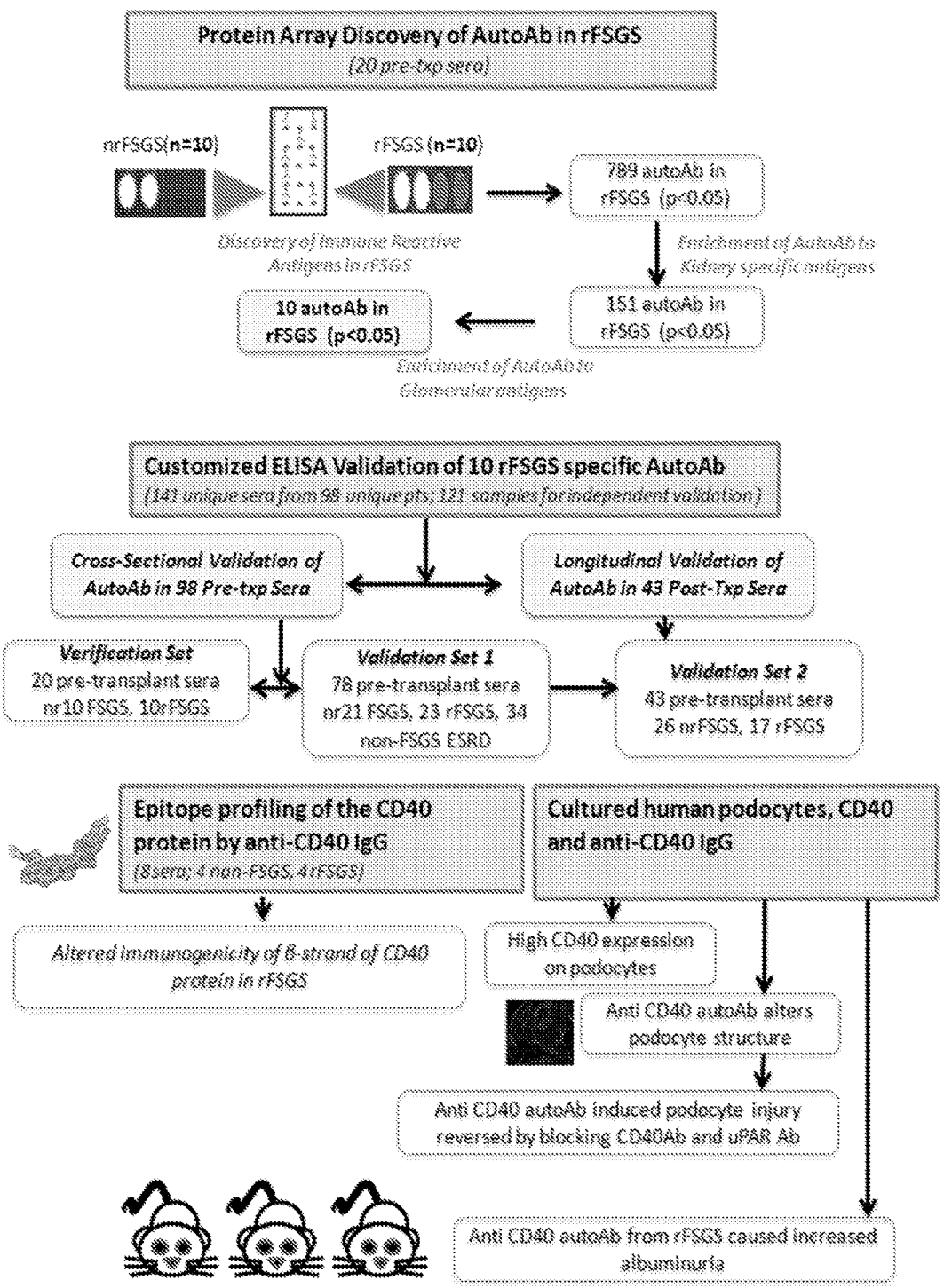
FIG. 1 is a schematic summarizing the study work flow and the samples for biomarker identification.

The invention described herein provides methods, compositions, and kits useful for identifying the risk an individual faces of developing nFSGS, rFSGS, predicting the onset of nFSGS, rFSGS, monitoring the progression of nFSGS, rFSGS, monitoring the regression of nFSGS, rFSGS, identifying a sub-population of patients who should be treated for nFSGS, rFSGS, identifying a sub-population of patients who should be continued to be treated for nFSGS, rFSGS, assessing efficacy of treatment for nFSGS, rFSGS, and/or identifying a sub-population of patients who should be monitored for nFSGS, rFSGS symptoms. As further detailed below, particular autoantibody biomarkers have been identified that may be utilized to accurately identify an individual who may develop primary or recurrent rFSGS. Such identification can be done pre-transplant or post-transplant.

The invention described herein also provides methods, compositions, and kits useful for the treatment of rFSGS. As further detailed below, such treatment may entail administering a blocking factor or a blocking antibody to those antigens which are elevated or altered in individuals with rFSGS.

Definitions

For purposes of interpreting this specification, the following definitions will apply and whenever appropriate, terms used in the singular will also include the plural and vice versa.

As used herein, a "blocking factor" is an agent that does not have a reaction when combined with an antigen, but prevents other antibodies from combining with that antigen.

As used herein, a "blocking antibody" is an antibody that does not have a reaction when combined with an antigen, but prevents other antibodies from combining with that antigen. A block antibody may be a full length antibody, an antibody fragment, a Fab fragment, a bi-specific antibody, a monoclonal antibody, a polyclonal antibody, a mouse antibody, a human antibody, or an antibody of any species.

As used herein, FSGS, is defined by heavy proteinuria with optional biopsy confirmation of FSGS with glomerular sclerosis and podocyte fusion and injury. The use of 'FSGS' covers native FSGS, primary FSGS as well as recurrent FSGS.

As used herein, recurrent FSGS (rFSGS), or recurrence of FSGS is defined by heavy proteinuria with optional biopsy confirmation of FSGS with glomerular sclerosis and podocyte fusion and injury without evidence of acute rejection, glomerulitis or allograft glomerulopathy. As used herein, a recurrent FSGS (rFSGS) individual or patient is defined as someone who had FSGS prior to kidney transplant and then developed a recurrence of FSGS (rFSGS) following kidney transplant.

As used herein, a non-recurrent FSGS (nrFSGS) individual or patient is defined as someone has FSGS prior to kidney transplant but does not develop FSGS following kidney transplant.

As used herein, a native FSGS (nFSGS) individual or patient is defined as someone who has FSGS (heavy proteinuria with optional biopsy confirmation of FSGS with glomerular sclerosis and podocyte fusion and injury) in their own kidney prior to transplant.

An individual "at risk" of developing FSGS may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of FSGS, as described herein and known in the art. A subject having one or more of these risk factors has a higher probability of developing FSGS than a subject without one or more of these risk factor(s). For example, in some embodiments, a subject "at risk" of developing recurrent FSGS shows a change in the level of expression of one or more autoantibodies as shown in Table 2.

An "individual" can be a "patient." A "patient," refers to an "individual" who is under the care of a treating physician. In another embodiment, the patient is an individual who has not been diagnosed with FSGS. In yet other embodiments, the patient is an individual who has been diagnosed with FSGS but has not had any treatment to address the FSGS.

The term "biological sample," as used herein, refers to a composition that is obtained or derived from an individual that contains a cellular and/or other molecular entity that is to be characterized and/or identified, for example based on physical, biochemical, chemical and/or physiological characteristics. In some embodiments, the biological sample is serum, blood, biological fluid or tissue from an individual.

"Predicting" and "prediction" as used herein does not mean that the event will happen with 100% certainty. Instead it is intended to mean the event will more likely than not happen. Acts taken to "predict" or "make a prediction" can include the determination of the likelihood that an event will be more likely than not to happen. Assessment of multiple factors described herein can be used to make such a determination or prediction.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of FSGS autoantibody analysis performed on biological samples from an individual, one may use the results to determine whether a specific therapeutic regimen should be performed for that individual.

The term "diagnosis" is used herein to refer to the identification or classification of a medical or pathological state, disease or condition. For example, "diagnosis" may refer to identification of FSGS, "Diagnosis" may also refer to the classification of a severity of FSGS. Diagnosis of FSGS may be made according to any protocol that one of skill of art (e.g., nephrologist) would use.

The term "aiding diagnosis" is used herein to refer to methods that assist in making a clinical determination regarding the presence, degree or other nature, of a particular type of symptom or condition of FSGS. For example, a method of aiding diagnosis of FSGS can include measuring the amount or detecting the presence or absence of one or more FSGS autoantibodies in a biological sample from an individual.

The term "prognosis" is used herein to refer to the prediction of the likelihood of the development of FSGS (including recurrence of FSGS). The predictive methods of the invention can be used clinically to make treatment decisions by choosing the most appropriate treatment modalities for any particular patient. The predictive methods of the present invention are valuable tools in predicting if and/or aiding in the diagnosis as to whether a patient is likely to develop FSGS, have recurrence of FSGS, and/or worsening of FSGS symptoms.

"Treatment" refers to clinical intervention in an attempt to alter the natural course of the individual and can be performed before, during, or after the course of clinical diagnosis or prognosis. Desirable effects of treatment include preventing the occurrence or recurrence of FSGS or a condition or symptom thereof, alleviating a condition or symptom of FSGS, diminishing any direct or indirect pathological consequences of FSGS, decreasing the rate of FSGS progression or severity, and/or ameliorating or palliating the FSGS. In some embodiments, methods and compositions of the invention are used on patient sub-populations identified to be at risk of developing FSGS. In some cases, the methods and compositions of the invention are useful in attempts to delay development of FSGS.

It is understood that aspects and embodiments of the invention described herein include "comprising," "consisting," and "consisting essentially of" aspects and embodiments. For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

As used herein, the term "peptide" may be used to refer to a natural or synthetic molecule comprising two or more amino acids linked by the carboxyl group of one amino acid to the alpha amino group of another. A peptide of the present invention is not limited by length, and thus "peptide" can be part of a longer polypeptide and/or of a protein or can refer to the longer polypeptide/protein itself. The term peptide can be used interchangeably with protein and/or polypeptide.

As used herein, the term "detect" refers to the quantitative measurement of undetectable, low, normal, or high serum concentrations of one or more biomarkers such as, for example, proteins, peptides and other biological molecules.

As used herein, the terms "quantify" and "quantification" may be used interchangeably, and refer to a process of determining the quantity or abundance of a substance in a sample (e.g., a biomarker), whether relative or absolute.

Reference to "about" a value or parameter herein includes (and describes) embodiments that are directed to that value or parameter per se. For example, description referring to "about X" includes description of "X." The term "about" is used to provide flexibility to a numerical range endpoint by providing that a given value may be "a little above" or "a little below" the endpoint without affecting the desired result. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As used in the specification and the appended claims, the singular forms "a," "an" and "the" include plural referents unless the context clearly indicates otherwise.

"Optional" or "optionally" means that the subsequently described event or circumstance can or cannot occur, and that the description includes instances where the event or circumstance occurs and instances where it does not.

General Techniques

Unless defined otherwise, technical and scientific terms used herein have the same meaning as commonly understood by one of ordinary skill in the art to which this invention belongs.

The practice of the present invention will employ, unless otherwise indicated, conventional techniques of protein biology, protein chemistry, molecular biology (including recombinant techniques), microbiology, cell biology, biochemistry, and immunology, which are within the skill of the art.

Collection of Biological Samples

Typically, a biological sample is collected from the individual. Any type of biological sample may be collected, including but not limited to serum, plasma, blood, urine, stools, mucus, saliva, and cerebrospinal fluid.

Testing of individuals for FSGS using the methods described herein may occur at any time prior to kidney transplantation or following kidney transplantation.

In one embodiment, the testing is done immediately before transplantation. In other embodiments the testing is done 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 1 month, 2 months, 3 months, 4 months, 5 months, 6 months, 7 months, 8 months, 9 months, 10 months, 11 months, or even 12 months prior to transplantation.

In another embodiment, the testing is done immediately after kidney transplantation. In other embodiments the testing is done 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 1 month, 2 months, 3 months, 4 months, 5 months, 6 months, 7 months, 8 months, 9 months, 10 months, 11 months, or even 12 months following transplantation.

Identification of rFSGS Autoantibodies

Methods for testing an individual for rFSGS may include detecting the difference in the concentration, expression, intracellular translocation, or activity of one or more autoantibodies associated with rFSGS present in a biological sample as compared to a healthy individual who does not develop rFSGS. Various systems and methods, as further described herein, can be used to identify, characterize, and quantify the autoantibodies. Non-limiting systems and methods are provided herein.

In one embodiment high density protein arrays can be used to identify autoantibodies that are differentially expressed between individuals with rFSGS or suspected of being at risk for developing rFSGS and healthy individuals.

In one embodiment, mass spectrometry can be used to identify autoantibodies that are differentially expressed between individuals with rFSGS or suspected of being at risk for developing rFSGS and healthy individuals. In such an embodiment, comparing multiple mass spectra from different biological samples, locating mass ions that are quantitatively different after using approaches to compensate for non-biological variability, isolating, and characterizing the autoantibody biomarker of interest can be used herein.

In another embodiment, capillary liquid chromatography can be used to identify autoantibodies that are differentially expressed between individuals with rFSGS or suspected of being at risk for developing rFSGS and healthy individuals. Those of skill in the art will appreciate that other techniques can be used to identify rFSGS autoantibodies.

Exemplary autoantibodies that were found to be associated with rFSGS are described in the examples and in Table 2. These rFSGS autoantibodies can also be used to identify patient sub-populations for treatment for rFSGS.

Identification of CD40 Binding

Methods for testing an individual for rFSGS may include detecting the binding of one or more antibodies to particular antigen epitopes associated with rFSGS present in a biological sample as compared to a healthy individual who does not develop rFSGS. Various systems and methods, as further described herein, can be used to identify, characterize, and quantify the epitopes of interest. Non-limiting systems and methods are provided herein.

In one embodiment peptide mapping, with a peptide microarray for example, can be used to identify epitopes that are differentially expressed between individuals with rFSGS or suspected of being at risk for developing rFSGS and healthy individuals.

In one embodiment, a method of predicting whether an individual will develop recurrent focal segmental glomerulosclerosis (rFSGS) comprises using an antibody that recognizes a particular epitope on an antigen, wherein the antigen is selected from the group consisting of consisting of CD40, PTPRO, CGB5, FAS, P2RY11, SNRPB2, APOL2, CCL19, MYLK, and RXRA. In some embodiments, this epitope is normally not present, or masked in patients who do not suffer from rFSGS, or have never suffered from any form of FSGS. In one embodiment, the particular epitope-recognizing antibody is a monoclonal antibody.

In one embodiment, a method of predicting whether an individual will develop recurrent focal segmental glomerulosclerosis (rFSGS) comprises using an antibody that recognizes a particular epitope on a CD40 antigen. In some embodiments, this epitope is normally not present, or masked in patients who do not suffer from rFSGS, or have never suffered from any form of FSGS. In a particular embodiment, the CD40 antibody is a monoclonal antibody. The CD40 antibody may recognize a portion of CD40's beta-strand region. In one particular embodiment, the CD40 antibody recognizes an epitope represented by the amino acids comprising ESEF (SEQ ID NO: 2). In another particular embodiment, the CD40 antibody recognizes an epitope represented by the amino acids comprising NSQCC (SEQ ID NO: 1).

Testing of Biological Samples

Biological samples taken from individuals can be used to identify autoantibodies or assess antibody binding that can be used to assess whether an individual has or will develop rFSGS (i.e., rFSGS autoantibodies; binding of a CD40 antibody to various epitopes). Various techniques of measuring autoantibodies and measuring the binding of antibodies are known to one of skill in the art.

Binding Agents and Methods of Using rFSGS Autoantibodies for Detecting rFSGS or Diagnosing the Risk of Developing rFSGS Binding agents of the invention may be used to identify autoantibodies present in the biological samples taken from an individual suspected of being at risk for developing FSGS, rFSGS, already suffering from rFSGS, or from a healthy individual. The binding agent can be one or more proteins, one or more peptides, one or more antibodies, one or more nucleic acids, or one or more nucleoproteins. The binding agent can comprise a plurality of binding sites for proteins, peptides, and autoantibodies. In one embodiment, the binding agent can be used to identify an autoantibody that would predict if an individual will develop rFSGS or has rFSGS, or is recovering from rFSGS. In such cases, the binding agent can be used to aid in the diagnosis of rFSGS or rFSGS status.

In the embodiments provided herein the binding of a binding agent to an autoantibody in a sample can be increased or decreased as compared to the binding of the binding agent to a reference standard, whereby the change in binding indicates the risk of developing rFSGS, or determining rFSGS status generally. As used herein, the reference standard can be a control of any type. For example the reference standard can comprise autoantibody data from a biological sample from and individual who has never suffered from FSGS, non-recurrent FSGS and/or recurrent FSGS. The reference standard can comprise autoantibody data from a biological sample from the same individual prior to developing any FSGS. The reference standard can comprise autoantibody data from biological samples from multiple individuals who have never suffered from FSGS, non-recurrent FSGS and/or recurrent FSGS Binding agents of the invention may be labeled or modified in some manner. For example binding agents may comprise a label. The binding agent may be covalently modified to incorporate the label. A label may include, but is not limited to a fluorescent label, an immunolabel, a magnetic label, a DNA label, a RNA label, a small molecule label, or a radio label.

A protein binding agent may be labeled or modified in some manner. For example protein binding agents may comprise a label. The protein binding agent may be covalently modified to incorporate the label. The label may include, but is not limited to a fluorescent label, an immunolabel, a magnetic label, a DNA label, a small molecule label, or a radio label.

A peptide binding agent may be labeled or modified in some manner. For example peptide binding agents may comprise a label. The peptide binding agent may be covalently modified to incorporate the label. The label may include, but is not limited to a fluorescent label, an immunolabel, a magnetic label, a DNA label, a small molecule label, or a radio label.

A nucleic acid binding agent may be labeled or modified in some manner. For example nucleic acid binding agents may comprise a label. The nucleic acid binding agent may be covalently modified to incorporate the label. The label may include, but is not limited to a fluorescent label, an immunolabel, a magnetic label, a DNA label, a small molecule label, or a radio label.

A nucleoprotein binding agent may be labeled or modified in some manner. For example nucleoprotein binding agents may comprise a label. The nucleoprotein binding agent may be covalently modified to incorporate the label. The label may include, but is not limited to a fluorescent label, an immunolabel, a magnetic label, a DNA label, a small molecule label, or a radio label.

The binding agent can bind one or more proteins, peptides, or ligands with a dissociation constant ($K_d$) of $10^{-15}$ M, $10^{-14}$ M, $10^{-13}$ M, $10^{-12}$ M, $10^{-11}$ M, $10^{-10}$ M, $10^{-9}$ M, $10^{-8}$ M, $10^{-7}$ M, $10^{-6}$ M, $10^{-5}$ M, $10^{-4}$ M, $10^{-3}$ M, or $10^{-2}$ M. In certain embodiments, the binding agent binds the one or more proteins, peptides, or ligands with a $K_d$ range of $10^{-12}$ M to $10^{-5}$ M, $10^{-10}$ M to $10^{-5}$ M, $10^{-8}$ M to $10^{-5}$ M, $10^{-7}$ M to $10^{-5}$ M, $10^{-10}$ M to $10^{-8}$ M, $10^{-9}$ M to $10^{-7}$ M, or $10^{-8}$ M to $10^{-6}$ M.

In one specific embodiment the binding agent can bind 1 autoantibody. In another embodiment the binding agent can bind 2 autoantibodies. In yet another embodiment, the binding agent can bind 3 autoantibodies. In related embodiments, the binding agent can bind 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, autoantibodies, up to a maximum of 30, 40, 50, 60, 70, 80, 90, or 100 autoantibodies. In one specific embodiment the binding agent can bind a maximum of 48 autoantibodies. In another specific embodiment the binding agent can bind any combination of 2, 3, 4, 5, 6, 7, 8, 9, 10 or more combinations of autoantibodies.

The rFSGS autoantibodies as described herein can be used to diagnose or aid in the diagnosis of individuals who are at risk of developing rFSGS. The rFSGS autoantibodies can also be used to identify the risk of developing rFSGS, predict the onset of rFSGS, monitor the progression of rFSGS, monitor the regression of rFSGS, identify a sub-population of patients who should be treated for rFSGS or continue to be treated for rFSGS, assess efficacy of treatment for rFSGS in individuals, and/or identify a sub-population of patients who should be monitored for rFSGS symptoms.

In one embodiment, the binding agents of the invention are selected from antibodies, autoantibodies, peptides, polypeptides, oligonucleotides, small molecules, ligands and the like. In a specific embodiment, binding agents of the invention comprise a fluorescent label, or a fluorescent immunolabel. In another specific embodiment, the binding agents of the invention comprise a magnetic label or magnetic immunolabel. In another specific embodiment, the binding agents of the invention comprise a radio label or magnetic radio label. In yet another embodiment, the binding agents are labeled with a oligonucleotide or a small molecule. In all embodiments, the binding agent may be covalently modified to incorporate the label.

In one embodiment a binding agent comprises an immune assay. An immunoassay can be used to detect, identify and/or quantify autoantibodies present in the biological samples taken from an individual suspected of being at risk for developing rFSGS and a healthy individual. In certain embodiments, the immunoassay can be an enzyme-linked immunosorbant assay (ELISA). Any immunoassay used herein can incorporate fluorescent, magnetic, or radio immunolabels.

In another embodiment, a binding agent comprises a diagnostic array. A diagnostic array can be used to detect, identify and/or quantify autoantibodies present in the biological samples taken from an individual suspected of being at risk for developing rFSGS and a healthy individual. The array can include a ligand, protein or antibody-coated substrate comprising a plurality of discrete, known regions on the substrate. The arrays can comprise particles, nanoparticles, beads, nanobeads, or other solid surfaces which can be porous or non-porous, and can range in size. In one embodiment, the diagnostic array does not comprise fluorescent particles. In another embodiment, the diagnostic array comprises fluorescent particles. In one embodiment, the diagnostic array does not comprise magnetic particles. In another embodiment, the diagnostic array comprises magnetic particles.

In a related embodiment, the binding agents of the invention comprise particles, nanoparticles, beads, nanobeads. In one embodiment, the nanoparticles, beads, or nanobeads are fluorescently labeled. In another embodiment, the nanoparticles, beads, or nanobeads are magnetically labeled. In another embodiment, the nanoparticles, beads, or nanobeads are radio labeled. In yet another embodiment, the nanoparticles, beads, or nanobeads are labeled with a oligonucleotide or a small molecule. In all embodiments, the binding agent may be covalently modified to incorporate the label.

In another embodiment, a binding agent comprises a magnetic-based protein assay component and/or nanotags. In such an embodiment, a magnetic multiplex protein assay is used to detect, identify, and/or quantify autoantibodies present in a biological sample with the use of magnetic nanotags. (Osterfeld et al., "Multiplex Protein Assays Based on Real-Time Magnetic Nanotag Sensing," PNAS, 105, 20637-20640 (published online Dec. 12, 2008) For example, a MagArray protein chip can be utilized for the diagnostic array. In this embodiment, autoantibody detection is used carried out in three steps. First, probes on the surface specifically bind to autoantibodies in the sample. Second, nanotag-labeled antibodies bind to the bound autoantibodies, forming sandwich-like structures. Finally, an external magnetic field is applied to the chip and the stray magnetic field produced by the nanotags is measured electrically to determine the presence of the target molecule in the sample.

In a related embodiment, the binding agents of the invention comprise nanotags. In one embodiment, the nanotags are fluorescently labeled. In another embodiment, the nanotags are magnetically labeled. In another embodiment, the nanotags are radio labeled. In yet another embodiment, the nanotags are labelled with a oligonucleotide or a small molecule. In all embodiments, the binding agent may be covalently modified to incorporate the label.

In another embodiment, carboxyl bead sets can be used to measure proteins, peptides of interest. Here, any autoantibody can be covalently attached to a stable microbead surface followed by fluorescent labeling and fluorescence intensity measurement. The VeraCode Technology by Illumina (Illumina Inc., Hayward, Calif.) allows to perform up to 48 immunoassays in varying combinations in a single reaction in a standard 96-well microplate.

In yet another embodiment proteins, peptides and autoantibodies can be measured by electrochemiluminesence ELISA. The multiplexed electrochemiluminesence ELISA platform by Meso Scale Discovery (MSD, Gaithersburg, Md.) is a high throughput multiplexed ELISA, custom designable, with the capability to simultaneously measure up to several analytes in the same well.

In another embodiment, functional protein-based assays can be used to detect differences in activity, binding, intracellular translocation, or post-translational processing of a autoantibody biomarker of interest. Such assays include competitive binding assays, western blot immunoblot assays, liposome immunoassays, and the like. In one specific embodiment, and by way of example only, an assay such as Invitrogen's ProtoArray® Microarray can be used to detect protein-protein interactions of interest. This array allows for profiling a biological sample such as serum or urine from an individual suspected for being at risk for rFSGS and can be used for identifying biologically relevant protein kinase substrates, small molecule binding partners, ubiquitin ligase substrates, and proteins interactors of antibodies.

The rFSGS autoantibodies can be detected by a binding agent with the functional parameter as described in the sections above. In other embodiments, the binding agent can be used to quantify rFSGS autoantibodies. This may be useful to predict the onset of rFSGS, predict the onset of rFSGS, the risk of developing rFSGS, to diagnose rFSGS, or to determine the severity of rFSGS symptoms.

One benefit of using the rFSGS autoantibodies as disclosed herein is that determination of the risk of developing rFSGS can be done with a high level of accuracy. Accuracy can be portrayed by sensitivity (the accuracy of the rFSGS positive patients correctly identified) and by specificity (the accuracy of the rFSGS negative patients correctly identified); positive predictive value (PPV) and negative predictive value (NPV) respectively.

In the embodiments provided herein, determination of the risk of developing rFSGS using the rFSGS autoantibodies for an individual suspected to be at risk for developing rFSGS is highly accurate for the detection or prediction of rFSGS. In the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% accuracy. Furthermore, in the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% accuracy for the detection, or prediction of rFSGS.

In the embodiments provided herein, determination of the risk of developing rFSGS using the rFSGS autoantibodies for an individual suspected to be at risk for developing rFSGS is highly sensitive for the detection or prediction of rFSGS. In the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% sensitivity. Furthermore, in the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% sensitivity for the detection, or prediction of rFSGS.

Furthermore in the embodiments provided herein, analysis of autoantibody biomarkers from an individual suspected to be at risk for developing rFSGS is highly specific for the detection or prediction of rFSGS. In the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% specificity. Furthermore, in the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% specificity for the detection, or prediction of rFSGS.

Moreover, in the embodiments provided herein, analysis of autoantibody biomarkers from an individual suspected to be at risk for developing rFSGS has a positive predictive value (PPV; the proportion of positive test results that are true positives/correct diagnoses) for the detection or prediction of rFSGS. In the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% PPV for the detection or prediction of rFSGS. Also, in the embodiments provided herein, analysis of biomarkers from an individual suspected to be at risk for developing rFSGS has a negative predictive value (NPV; the proportion of subjects with a negative test result who are correctly diagnosed) for the detection or prediction of rFSGS. In the embodiments provided herein, the methods provide at least 60%, at least 65%, at least 70%, at least 75%, at least 80%, at least 85%, at least 90%, at least 95%, at least 96%, at least 97%, at least 98%, at least 99%, or 100% NPV, for the detection or prediction of rFSGS.

In the embodiments provided herein, the analysis of biomarkers from an individual suspected to be at risk for developing rFSGS provides an area under the curve (AUC), which is a statistical measurement of the probability of the detection of rFSGS, or a statistical measurement of the probability for predicting the development of rFSGS. In the embodiments provided herein, the methods provide an AUC of at least 0.80, at least 0.81, at least 0.82, at least 0.83, at least 0.84, at least 0.85, at least 0.86, at least 0.87, at least 0.88, at least 0.89, at least 0.90, at least 0.91, at least 0.92, at least 0.93, at least 0.94, at least 0.95, at least 0.96, at least 0.97, at least 0.98, at least 0.99, and 1.0 for the detection of rFSGS or for predicting the development of rFSGS.

The analysis of biological samples taken from either an individual suspected to be at risk for developing rFSGS or from a healthy individual include testing for only 1, testing for combinations of 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more autoantibodies, up to a maximum of 30, 40, 50, 60, 70, 80, 90, or 100 rFSGS autoantibodies disclosed herein.

In one embodiment, the analysis of biomarkers from an individual suspected to be at risk for developing rFSGS comprises detecting an increase or decrease in at least one autoantibody selected from Table 2. In such an embodiment, the risk for developing rFSGS can comprise a change in the autoantibody presence of concentration of CD40, PTPRO, CGB5, FAS, P2RY11, SNRPB2, APOL2, CCL19, MYLK, or RXRA.

In another embodiment, the analysis can include testing for up to any one or combination (of 2 or more, or of 3 or more) of the 10 autoantibodies as disclosed in Table 1; or any one or combination (of 2 or more, or 3 more more) of the 151 autoantibodies found to be elevated in rFSGS, as described in the Examples. Combinations of the autoantibodies of Table 2 can provide a minimal set of autoantibodies for differentiating the risk of developing rFSGS from healthy individuals.

The rFSGS antibodies of the invention can also be used to identify a patient sub-population of individuals who are at risk for rFSGS for treatment purposes. In some embodiments, this sub-population is monitored for development, progression, or regression of rFSGS symptoms.

In some embodiments, this sub-population is treated for rFSGS prior to or at the onset of rFSGS symptoms. This sub-population of patients can be monitored for various physiological parameters known to a treating physician at all stages to ensure their safety. In some cases, the monitoring is done to determine if the treatment should be continued or to see if the treatment is efficacious.

Therefore, using the rFSGS autoantibodies of the invention and the methodology described herein, one of skill in the art can determine the risk of developing rFSGS, can determine the onset of rFSGS, monitor the progression of rFSGS, monitoring the regression of rFSGS, identify a sub-population of patients who should be treated for rFSGS or continue to be treated for rFSGS, assess efficacy of treatment for rFSGS in individuals, and/or identify a sub-population of patients who should be monitored for rFSGS symptoms.

Treatment of nFSGS, rFSGS, and Other Proteinuric Renal Diseases

The present invention provides methods and compositions for the treatment of primary FSGS, recurrent FSGS, proteinuric diseases in general such as minimal change disease, glomerular nephritis, membrano-proliferative glomerular nephritis (membranous), IgA glomerular nephritis (membranous), and steroid-resistant minimal change nephrotic syndrome.

In one embodiment, the invention provides a method of preventing an individual from developing native FSGS, or rFSGS comprising administering to the individual a blocking factor. In one embodiment, the factor blocks the binding of an autoantibody to a target selected from the group consisting of CD40, PTPRO, CGB5, FAS, P2RY11, SNRPB2, APOL2, CCL19, MYLK, and RXRA. In one embodiment, the target is CD40. In one embodiment, the blocking factor is a blocking antibody. In one embodiment, the target of the blocking antibody is selected from the group consisting of CD40, PTPRO, CGB5, FAS, P2RY11, SNRPB2, APOL2, CCL19, MYLK, and RXRA. In one embodiment, the target is CD40. In one embodiment the antibody is a CD40 blocking antibody. In one embodiment, the antibody is a PTPRO blocking antibody. In one embodiment, the individual is not suffering from any type of FSGS at the time of treatment.

In one embodiment, the invention provides herein embodiments for the treatment of rFSGS as well as for the prevention of FSGS or rFSGS.

In the treatment and prevention embodiments provided herein, the prevention treatment may be carried out pre-transplant (prior to the individual undergoing kidney transplantation) or post-transplant (after the individual has undergone kidney transplantation).

In one embodiment a method of treating an individual who suffers from rFSGS comprises administering to the individual a blocking factor.

In one embodiment a method of treating an individual who suffers from nFSGS comprises administering to the individual a blocking factor.

In another embodiment a method of preventing an individual from developing FSGS or rFSGS comprises administering to the individual a blocking factor.

Blocking factors of the invention block the binding of an autoantibody to a target selected from the group consisting of CD40, PTPRO, CGB5, FAS, P2RY11, SNRPB2, APOL2, CCL19, MYLK, and RXRA. In one specific embodiment, the target is CD40.

Blocking factors of the invention may be blocking antibodies. In one embodiment, the blocking factor is selected from the group consisting of CD40, PTPRO, CGB-5, FAS, P2RY11, SNRPB2 and APOL2. In one specific embodiment, the target is CD40.

Combination Treatments for the Treatment of nFSGS, rFSGS, and Other Proteinuric Renal Diseases The present invention provides methods and compositions for combination treatments of primary FSGS, recurrent FSGS, proteinuric diseases in general, minimal change disease, glomerular nephritis, membrano-proliferative glomerular nephritis (membranous), IgA glomerular nephritis (membranous), and steroid-resistant minimal change nephrotic syndrome, using known treatment paradigms.

In some embodiments the treatment further comprises treating the individual with other known rFSGS treatment paradigms. For example, in one embodiment the treatment comprises administering a blocking factor, and carrying out plasmapheresis. The treatment can also include cyclophosphamide. In another embodiment the treatment comprises administering a blocking factor and rituximab. In another embodiment, the treatment comprises carrying out antibody immuneadsorption.

In some embodiments the treatment further comprises treating the individual with other known native FSGS treatment paradigms. For example, in one embodiment the treatment comprises administering a blocking factor, and carrying out plasmapheresis. The treatment can also include cyclophosphamide. In another embodiment the treatment comprises administering a blocking factor and rituximab. In another embodiment, the treatment comprises carrying out antibody immuneadsorption.

The following examples are provided for illustrative purposes. These are intended to show certain aspects and embodiments of the present invention but are not intended to limit the invention in any manner.

Methods of Administration

In some embodiments, blocking factor or antibody provided herein is administered intravenously, intramuscularly, subcutaneously, topically, orally, transdermally, intraperitoneally, intraorbitally, by implantation, by inhalation, intrathecally, intraventricularly, or intranasally. An effective amount of the blocking factor or antibody may be administered for the treatment of any type of FSGS. The appropriate dosage of the blocking factor or antibody may be determined based on the type of FSGS to be treated, the type of the blocking factor or antibody, the severity and course of the FSGS, the clinical condition of the individual, the individual's clinical history and response to the treatment, and the discretion of the attending physician.

Kits for the Treatment, Prevention, Diagnosis, Detection, or Prediction of Native FSGS, rFSGS, and Other Proteinuric Renal Diseases The invention further provides for assay kits for the treatment, prevention, diagnosis, detection and prediction of native FSGS, rFSGS, and other proteinuric diseases.

In one embodiment, a kit comprises reagents for detecting an autoantibody in a biological sample from an individual. The reagents can comprise binding agents of the invention. The binding agents and reagents found in the kit may be labeled. They may be labeled, for example, with a fluorescent label, a radiolabel, an immunolabel, a magnetic label, a small molecule label, a DNA- or RNA-based label, and/or any labels known to those in the art. In all embodiments, the binding agent may be covalently modified to incorporate the label. The kit further comprises a composition comprising one or more solid surfaces that contain at least binding agent, capable of specifically binding an autoantibody biomarker (or combinations thereof) of interest in the biological sample. The kit also comprises instructions for the use of the assay.

In another embodiment a diagnostic assay kit comprises reagents for detecting an autoantibody in a biological sample from an individual; a composition comprising a solid surface that contains a binding agent for an autoantibody selected from the group consisting of CD40, PTPRO, CGB5, FAS, P2RY11, SNRPB2, APOL2, CCL19, MYLK, and RXRA; and instructions for use of the assay. For example, the solid surface could contain a binding agent for a CD40 autoantibody. The binding agent can be selected from a CD40 ligand, a PTPRO ligand, a CGB5 ligand, a FAS ligand, a P2RY11 ligand, a SNRPB2 ligand, an APOL2 ligand, a CCL19 ligand, a MYLK ligand, and a RXRA ligand. In one specific embodiment, the binding agent is a CD40 ligand.

In another embodiment, the invention provides an assay kit comprising a composition comprising a solid surface that contains a binding agent for a CD40 epitope; reagents for detecting a CD40 epitope in a biological sample from an individual; and instructions for use of the assay. In one embodiment, the binding agent is a CD40 antibody that recognizes a specific epitope of interest.

In another embodiment the kit comprises any antibody or blocking factor for treatment and further comprises a pharmaceutically acceptable excipient. In one embodiment, the factor blocks the binding of an autoantibody to a target selected from the group consisting of CD40, PTPRO, CGB5, FAS, P2RY11, SNRPB2, APOL2, CCL19, MYLK, and RXRA. In one embodiment, the target is CD40. In one embodiment, the blocking factor is a blocking antibody. In one embodiment, the target of the blocking antibody is selected from the group consisting of CD40, PTPRO, CGB5, FAS, P2RY11, SNRPB2, APOL2, CCL19, MYLK, and RXRA. In one embodiment, the target is CD40. In one embodiment the antibody is a CD40 blocking antibody. In one embodiment, the antibody is a PTPRO blocking antibody. In one embodiment, the individual is not suffering from any type of FSGS at the time of treatment.

The present application provides kits comprising any one or more of the antibody or a blocking factor described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

Pharmaceutical Compositions

The present application provides compositions comprising the antibodies and blocking factors including pharmaceutical compositions comprising any one or more of the antibodies or blocking factors described herein with one or more pharmaceutically acceptable excipients. In some embodiments the composition is sterile. The pharmaceutical compositions generally comprise an effective amount of an antibody or blocking factor.

Articles of Manufacture

The present application also provides articles of manufacture comprising any one of the antibody or blocking factor compositions or kits described herein. Examples of an article of manufacture include vials (including sealed vials).

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

Exemplary Embodiments

1. A method of predicting whether an individual will develop recurrent focal segmental glomerulosclerosis (rFSGS) comprising: a. contacting a biological sample from the individual with a binding agent; and b. detecting the binding of the binding agent to at least one autoantibody in the sample, wherein the autoantibody is selected from the autoantibodies listed in Table 2; wherein the binding of the binding agent to the autoantibody in the sample is increased as compared to the binding of the binding agent to a reference standard, whereby the increase in binding indicates the risk of developing rFSGS.

2. A method of predicting whether an individual will develop native FSGS, minimal change disease, glomerular nephritis, membrano-proliferative glomerular nephritis (membranous), or IgA glomerular nephritis (membranous) comprising: a. contacting a biological sample from the individual with a binding agent; and b. detecting the binding of the binding agent to at least one autoantibody in the sample, wherein the autoantibody is selected from the autoantibodies listed in Table 2; wherein the binding of the binding agent to the autoantibody in the sample is increased as compared to the binding of the binding agent to a reference standard, whereby the increase in binding indicates the risk of developing native FSGS, minimal change disease, glomerular nephritis, membrano-proliferative glomerular nephritis (membranous), or IgA glomerular nephritis (membranous).

3. The method of embodiment 1 or 2 wherein the biological sample is serum.

4. The method of embodiment 1 or 2 wherein the reference standard comprises autoantibody data from individuals who have never suffered from FSGS, non-recurrent FSGS, or rFSGS.

5. The method of embodiment 1 or 2 wherein the autoantibody is selected from the group consisting of antibodies to CD40, PTPRO, CGB5, FAS, P2RY11, SNRPB2, APOL2, CCL19, MYLK, and RXRA.

6. The method of embodiment 1 or 2 wherein the binding agent is a selected from a CD40 ligand, a PTPRO ligand, a CGB5 ligand, a FAS ligand, a P2RY11 ligand, a SNRPB2 ligand, an APOL2 ligand, a CCL19 ligand, a MYLK ligand, and a RXRA ligand.

7. The method of embodiment 1 or 2 wherein the autoantibody is an antibody to CD40 or PTPRO.

8. The method of embodiment 1 or 2 wherein the binding agent binds the autoantibody with a Kd of 10-12 M to 10-5 M.

9. The method of embodiment 1 or 2 wherein the increase in binding indicates the risk of developing FSGS to at least an 80% degree of accuracy.

10. The method of embodiment 1 or 2 wherein the binding agent-autoantibody binding is determined using an ELISA.

11. The method of embodiment 1 or 2 wherein the method is carried out after the individual has undergone kidney transplantation.

12. The method of embodiment 1 or 2 wherein the method is carried out prior to when the individual has undergone any kidney transplantation.

13. The method of embodiment 12 wherein the method is carried out 1 day prior to when the individual undergoes kidney transplantation.

14. A method of predicting whether an individual will develop recurrent focal segmental glomerulosclerosis (rFSGS) comprising: a. contacting a biological sample from the individual with a CD40 antibody; and b. detecting the binding of the antibody to a CD40 antigen;
wherein the binding of the CD40 antibody to the CD40 antigen in the sample is increased as compared to the binding of the CD40 antibody to a reference standard, whereby the increase in binding indicates the risk of developing rFSGS.

15. A method of predicting whether an individual will develop native FSGS, minimal change disease, glomerular nephritis, membrano-proliferative glomerular nephritis (membranous), or IgA glomerular nephritis (membranous) comprising: a. contacting a biological sample from the individual with a CD40 antibody; and b. detecting the binding of the antibody to a CD40 antigen; wherein the binding of the CD40 antibody to the CD40 antigen in the sample is increased as compared to the binding of the CD40 antibody to a reference standard, whereby the increase in binding indicates the risk of developing native FSGS, minimal change disease, glomerular nephritis, membrano-proliferative glomerular nephritis (membranous), or IgA glomerular nephritis (membranous).

16. The method of embodiment 14 or 15 wherein the biological sample is serum.

17. The method of embodiment 14 or 15 wherein the CD40 antibody recognizes a particular epitope of CD40.

18. The method of embodiment 14 or 15 wherein the CD40 antibody is a monoclonal antibody.

19. The method of embodiment 14 or 15 wherein the CD40 antibody recognizes a portion of CD40's beta-strand region.

20. The method of embodiment 14 or 15 wherein the CD40 antibody recognizes an epitope represented by a stretch of amino acids comprising ESEF (SEQ ID NO: 2).

21. The method of embodiment 14 or 15 wherein the CD40 antibody recognizes an epitope represented by a stretch of amino acids comprising NSQCC (SEQ ID NO: 1).

22. The method of embodiment 14 or 15 wherein the reference standard comprises CD-40 binding data from individuals who have never suffered from FSGS, non-recurrent FSGS, or rFSGS.

23. The method of embodiment 14 or 15 wherein the increase in binding indicates the risk of developing to at least an 80% degree of accuracy.

24. The method of embodiment 14 or 15 wherein the method is carried out after the individual has undergone kidney transplantation.

25. The method of embodiment 14 or 15 wherein the method is carried out prior to when the individual has undergone any kidney transplantation.

26. The method of embodiment 25 wherein the method is carried out 1 day prior to when the individual undergoes kidney transplantation.

27. A method of treating an individual who suffers from rFSGS comprising administering to the individual a blocking factor.

28. A method of treating an individual who suffers from native FSGS, minimal change disease, glomerular nephritis, membrano-proliferative glomerular nephritis (membranous), or IgA glomerular nephritis (membranous) comprising administering to the individual a blocking factor.

29. The method of embodiment 27 or 28 wherein the factor blocks the binding of an autoantibody to a target selected from the group consisting of CD40, PTPRO, CGB5, FAS, P2RY11, SNRPB2, APOL2, CCL19, MYLK, and RXRA.

30. The method of embodiment 29 wherein the target is CD40 or PTPRO.

31. The method of embodiment 27 or 28 wherein the blocking factor is a blocking antibody.

32. The method of embodiment 31 wherein the target of the blocking antibody is selected from the group consisting of CD40, PTPRO, CGB5, FAS, P2RY11, SNRPB2, APOL2, CCL19, MYLK, and RXRA.

33. The method of embodiment 32 wherein the target is CD40 or PTPRO.

34. The method of embodiment 27 or 28 the method is carried out after the individual has undergone kidney transplantation.

35. The method of embodiment 27 or 28 further comprising treating the individual with plasmapheresis.

36. The method of embodiment 27 or 28 further comprising treating the individual with antibody immuadsorption.

37. The method of embodiment 27 or 28 further comprising treating the individual with rituximab.

38. A method of preventing an individual from developing rFSGS comprising administering to the individual a blocking factor.

39. A method of preventing an individual from developing native FSGS, minimal change disease, glomerular nephritis, membrano-proliferative glomerular nephritis (membranous), or IgA glomerular nephritis (membranous) comprising administering to the individual a blocking factor.

40. The method of embodiment 38 or 39 wherein the factor blocks the binding of an autoantibody to a target selected from the group consisting of CD40, PTPRO, CGB5, FAS, P2RY11, SNRPB2, APOL2, CCL19, MYLK, and RXRA.

41. The method of embodiment 40 wherein the target is CD40 or PTPRO.

42. The method of embodiment 38 or 39 wherein the blocking factor is a blocking antibody.

43. The method of embodiment 42 wherein the target of the blocking antibody is selected from the group consisting of CD40, PTPRO, CGB5, FAS, P2RY11, SNRPB2, APOL2, CCL19, MYLK, and RXRA.

44. The method of embodiment 43 wherein the target is CD40 or PTPRO.

45. The method of embodiment 38 or 39 wherein the individual is not suffering from rFSGS at the time of treatment.

46. The method of embodiment 38 or 39 wherein the method is carried out after the individual has undergone kidney transplantation.

47. The method of embodiment 38 or 39 wherein the method is carried out before the individual has undergone any kidney transplantation.

48. The method of embodiment 38 or 39 further comprising treating the individual with plasmapheresis.

49. The method of embodiment 38 or 39 further comprising treating the individual with immuneadsoprtion.

50. The method of embodiment 38 or 39 further comprising treating the individual with rituximab.

51. An assay kit comprising: a. reagents for detecting an autoantibody in a biological sample from an individual; b. a composition comprising a solid surface that contains a binding agent for an autoantibody selected from the group consisting of CD40, PTPRO, CGB5, FAS, P2RY11, SNRPB2, APOL2, CCL19, MYLK, and RXRA; and c. instructions for use of the assay.

52. The kit of embodiment 51 comprising a solid surface containing a binding agent for a CD40 autoantibody or PTPRO autoantibody.

53. The kit of embodiment 51 wherein the binding agent is a selected from a CD40 ligand, a PTPRO ligand, a CGB5 ligand, a FAS ligand, a P2RY11 ligand, a SNRPB2 ligand, an APOL2 ligand, a CCL19 ligand, a MYLK ligand, and a RXRA ligand.

54. The kit of embodiment 51 wherein the binding agent is a CD40 ligand or PTPRO ligand.

55. An assay kit comprising: a. a composition comprising a solid surface that contains a binding agent for a CD40 epitope; b. reagents for detecting an CD40 epitope in a biological sample from an individual; c. instructions for use of the assay.

56. The kit of embodiment 55 wherein the binding agent is a CD40 antibody.

57. The kit of embodiment 56 wherein the CD40 antibody recognizes an epitope represented by a stretch of amino acids comprising ESEF (SEQ ID NO: 2) or a stretch of amino acids comprising NSQCC (SEQ ID NO: 1).

EXAMPLES

Example 1

Materials and Methods

Patients and Samples:

141 sera samples, obtained prior to and one year after renal transplantation, were processed from 98 unique renal transplant patients, enrolled from 5 international transplant centers: Transplantation Renale Adulte, Hopital Necker-Enfants Malades (Paris, France); John Hopkins Hospital (Baltimore, Mass.), and Nephrology and Renal Transplantation, University Hospitals Leuven (Leuven, Belgium). The study was approved by the Institutional Review Board of California Pacific Medical Center, Stanford University, Necker, John Hopkins and Leuven for biobanking and samples analysis.

Immune Response Biomarker Profiling by Protein Microarrays and ELISA Validation:

The ProtoArray® human protein microarray was used for profiling serum IgG autoantibody in 20 pre-transplant sera from 10 patients with and without rFSGS. The Meso Scale Discovery® (MSD) technology was used for customized ELISA validation for elevated antibody titers in rFSGS to FAS, CD40, CCL19, MYLK, CGB5, SNRBP2, RXRA, P2RY11, PTPRO, and APOL2.

Podocyte Cell Cultures:

Normal human podocytes were cultured in the presence of patients' sera and lysates for western blotting, using a mouse monoclonal antibody against CD40 and GAPDH [7]. Cultured human podocytes were treated for 24 hrs with rFSGS sera, with high level of CD40 autoantibody and purified CD40 IgG from rFSGS patients (n=4). Cellular F-actin expression and distribution was evaluated by Phalloidin staining. Recombinant SuPAR protein [7] and small molecule that blocks beta 3 integrin activity, 5cycloRGDfV, were each used at 1 mcg/ml for additional treatment of cultured podocytes. Monoclonal CD40 antibody was given at a differential ratio (1:1 and 3:1) of CD40 autoantibody to assess the competitive nature of the two Ab.

Pathogenecity of Anti-CD40 Antibody by In Vivo Mouse Study:

The investigation on the role of anti-CD40 antibody (CD40 IgG) on generating proteinuria was tested in vivo. This was done in 2 phases. In the first experiment, 5 µg of CD40 autoantibody isolated from sera of patients was injected with and without rFSGS, into B6 mice (n=5 in each group). To control for the short half-life of injected IgG antibody [22] CD40 autoantibody was injected twice, 48 hours apart. Urine albumin to ceatinine ratio (UACR) was calculated on days 1-8, with the CD40 autoantibody injection occurring on Days 1 and 3. In the second experiment, C57BL/6 mice, female, age 10 weeks, with body weight ranging 18-20 g were used. Eight mice were randomly chosen to receive CD40 autoantibody i.v from recurrent FSGS patients, while 7 were to receive CD40 autoantibody from non-recurrent FSGS. The dose was referred from the relative amount of CD40 autoantibody in recurrent FSGS patients versus that in non-recurrent FSGS patients, which is about 4:1. The calculated final concentration was 8 µg/ml for CD40 autoantibody from recurrent FSGS, 2 µg/ml for non-recurrent FSGS CD40 autoantibody. Injection of CD40 autoantibody was given 6 times, every other day. Six hours after the last dose of CD40 autoantibody, recombinant human suPAR (R&D) protein was given i.v. at 5 µg/ml to all mice in order to analyze the effect of suPAR. 24 hr after the last dose of CD40 autoantibody, blocking mouse monoclonal CD40 antibody (Santa Cruz Biotechnology, Inc, Santa Cruz, Calif.) was administered i.p at a dose of 3 µg. Urine was collected before and every day after the first injection of CD40 autoantibody to analyze urinary albumin with a mouse albumin ELISA kit (Bethyl Laboratories, Inc, Montgomery, Tex.) and creatinine (Cayman Chemical Company, Ann Arbor, Mich.) concentration. The OD value was quantified with Image J program. Proteinuria is expressed as albumin (mg)/creatinine (g) ratio.

Epitope Profiling of Anti-CD40 IgG:

The PepStar® human peptide microarray (JPT, Berlin, Germany), with 15mer peptide with 4 overlapping aminoacids, was used to map reactive epitopes of CD40 by probing it with sera samples from patients with (n=4) and without rFSGS (n=4). Human IgGs were used as positive control and mouse and rabbit IgGs were used as negative control.

Statistical Analysis:

Demographical data statistical analysis was performed with Mann-Withney, one way-ANOVA and Fischer exact tests. ELISA validation results were analyzed with a Mann-Whitney test. All statistical calculation was performed using GraphPad Prism® (La Jolla, Calif.). Nominal logistic regression modeling was performed and antibodies were selected by stepwise methods with significant p-values <0.05. Receiver operating characteristics (ROC) curves were generated from the ELISA data using GraphPad Prism® (La Jolla, Calif.).

Example 2

Identification of Antibodies Associated with rFSGS after Renal Transplantation

Figure 2:
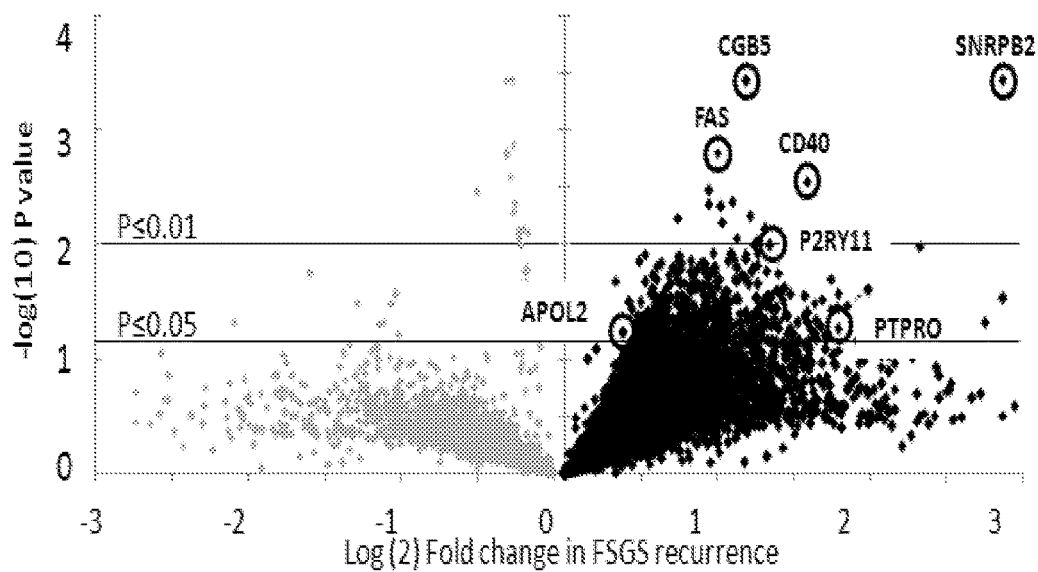
FIG. 2 shows the significant autoantibodies in sera samples collected immediately before transplantation in patients with (n=10, gray dots) and without (n=10, black dots) rFSGS after transplantation. The most significant autoantibodies selected for and validated by ELISA are labeled. The plot maps significance versus fold-change on the y- and x-axes, respectively.

To identify potential autoantibodies associated with rFSGS, a discovery set of pre-transplant sera was used. The discovery set was from from 20 unique patients with biopsy confirmed diagnosis of FSGS as their cause of End Stage Renal disease (ESRD), of which 10 had progressed to rFSGS within the first post-transplant year (mean time to recurrence 36 days) and 10 FSGS patients had not had recurrence of proteinuria or histological disease after transplantation (nrFSGS). At transplant, these two groups of patients were indistinguishable regarding demographical or clinical parameters (Table 1). Recurrence was defined by heavy proteinuria with biopsy confirmation of FSGS with glomerular sclerosis and podocyte fusion and injury without evidence of acute rejection, glomerulitis or allograft glomerulopathy. Sera samples were assayed on high-density protein microarrays (Protoarray v5.0; Life Technologies). FIG. 1 summarizes the study. IgG antibodies against a total of 789 unique antigens were increased in the recurrent group at transplant (p<0.05). In contrast, only a small number of IgG antibodies against 78 unique antigens showed a significant decrease in recurrent patients. FIG. 2 shows the Volcano plot of IgG profiles in serum from rFSGS and nrFSGS patients. These data suggest that rFSGS is associated with a strong signature of newly recognized autoantibody after kidney transplantation.

For biomarker selection, the data were filtered to maximize for fold increase (>2) and signal intensity twice above the background threshold (>1000), which resulted in a selection of 151 IgG antibodies for further analysis. The pathogenic relevance of the antibodies were additionally filtered; based on the fact that the hallmark of FSGS is glomerular injury. The filtering was for selection of antibodies to antigens that would be highly expressed in the renal glomerulus using previously published integrative antibiomic analysis [19], where cross-mapping of significant autoantibody targets with kidney compartment gene expression data was performed [19]. The analysis revealed that most of these 151 autoantibodies were specific to proteins whose transcripts are enriched in specific compartments of the kidney: in the glomerular compartment (p=0.02), in the outer cortex (p=0.01), in the pelvis (p=0.02), and in the papillary tip (p=0.01). Pathway analysis for the mechanisms of injury by this antibody panel (Ingenuity Pathway Analysis software showed a response relating to antigen presentation (p=$5.97E^{-6}$), increased inflammatory (p=$5.97E^{-6}$), and cell death (p-value=$6.03E^{-5}$). From the 151 identified Ab, 10 IgAb were selected for further validation by ELISA, based on their fold change, the inferred glomerular expression of the antigen, and functional relevance (implication in inflammatory disease, and kidney injury).

Example 3

Figure 3:
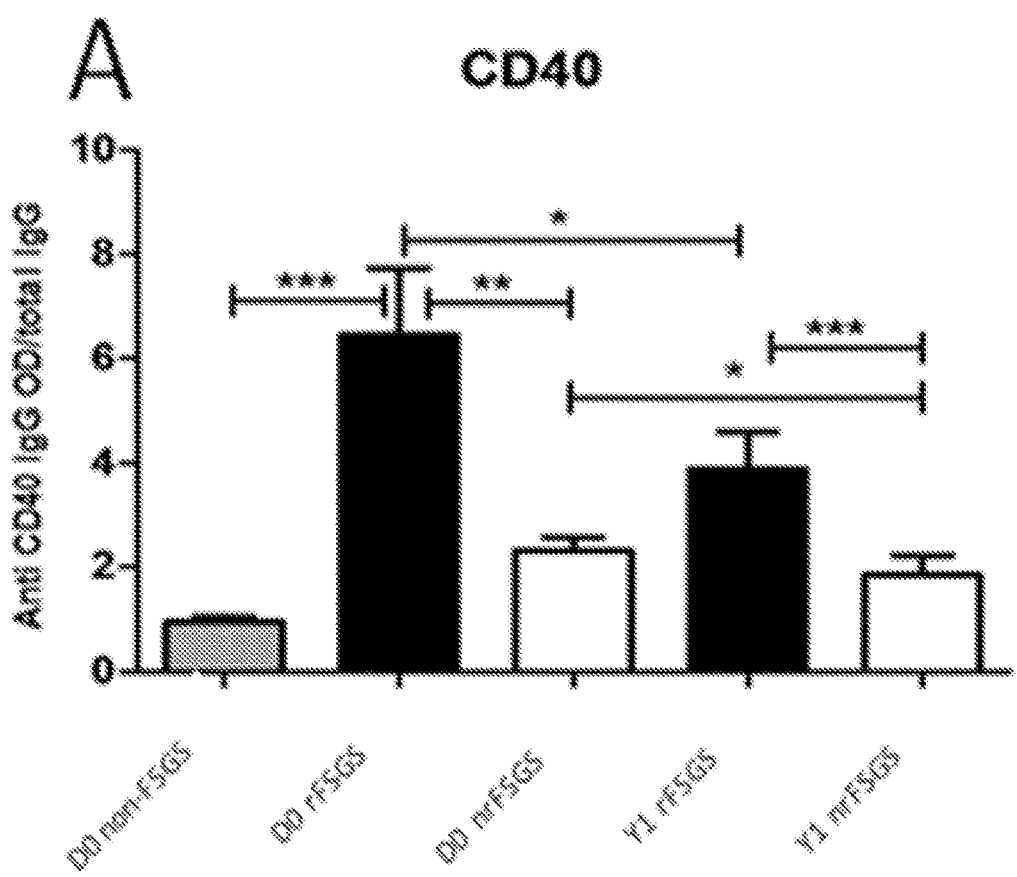
FIG. 3 shows the validation of elevated autoantibodies in rFSGS by customized ELISA assays. Panels [A-G]: ELISA assays were developed and optimized to validate rFSGS specific autoantibodies in results. Black bars correspond to serum samples collected immediately before transplantation (Day 0, n=28) and at one year post-transplantation (Year 1, n=26) in patients who experienced rFSGS. White bars correspond to serum samples collected immediately before transplantation (Day 0, n=31) and at one year post-transplantation (Year 1, n=17) in patients who did not experience rFSGS during the first year. Gray bars represent non-FSGS control samples (n=34). Y-axis represents the ratio of the OD (Optical Density) from Meso Scale Discovery (MSD®) ELISA assay over total IgG in mg/dL for each patient. (*: p value <0.05; : p value <0.001; *: p value <0.0001). Panel [H] shows the ROC analysis using three fitted logistic regression models. The outcome is recurrence vs non-recurrence and the independent predictors are seven genes CD40, FAS, PTPRO, P2RY11, CGB5, SNRPB2, APOL2. These predictors are log-transformed to correct for their skewness. Three logistic regressions were fitted. Model 1: Recurrence/Nonrecurrence vs CD40, FAS, PTPRO, P2RY11, CGB5, SNRPB2, APOL2. AUC=0.9 (CI: 0.81-0.99). Model 2: Recurrence/Nonrecurrence vs CD40, PTPRO, CGB5. AUC=0.82 (CI: 0.70-0.95). Model 3: Recurrence/Nonrecurrence vs CD40. AUC=0.77 (CI:0.63-0.92)
Figure 3:
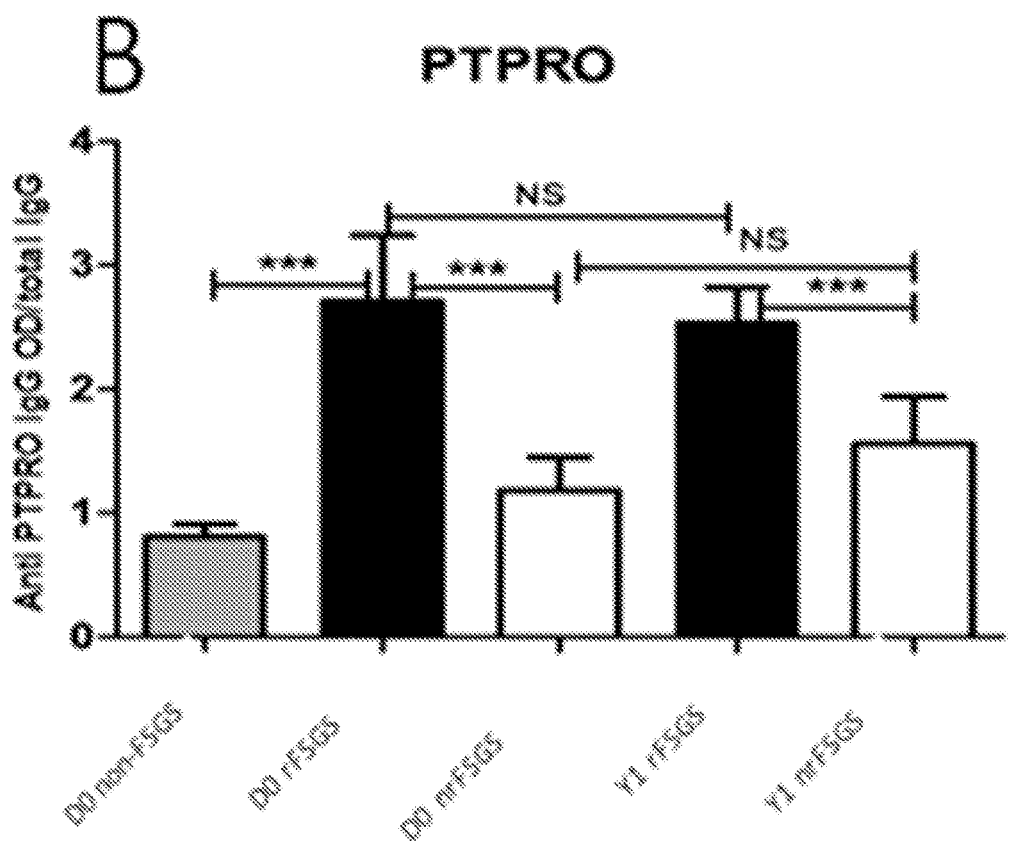
Figure 3:
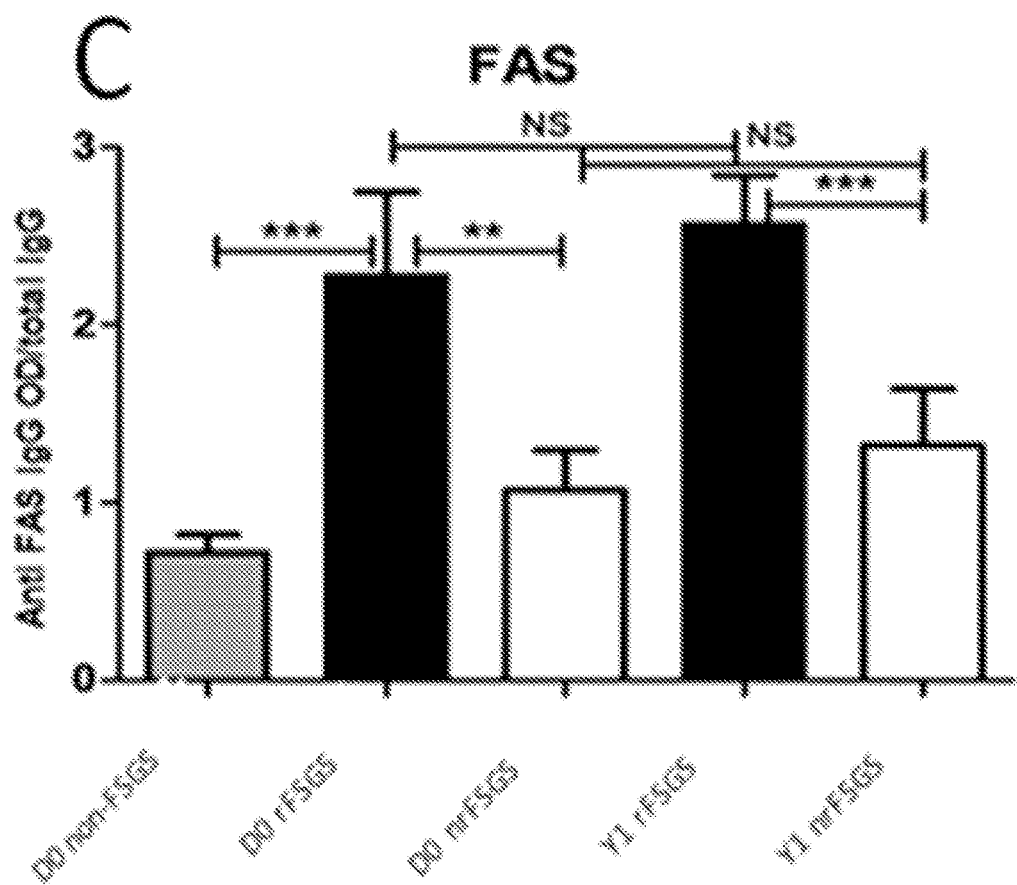
Figure 3:
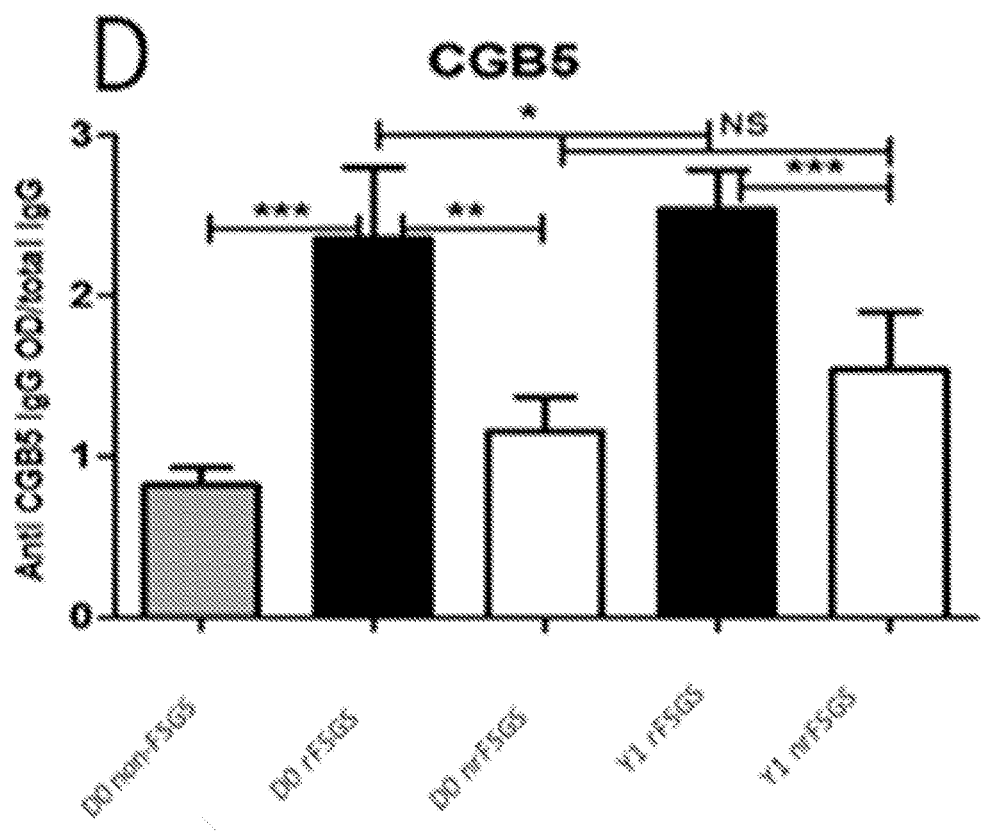
Figure 3:
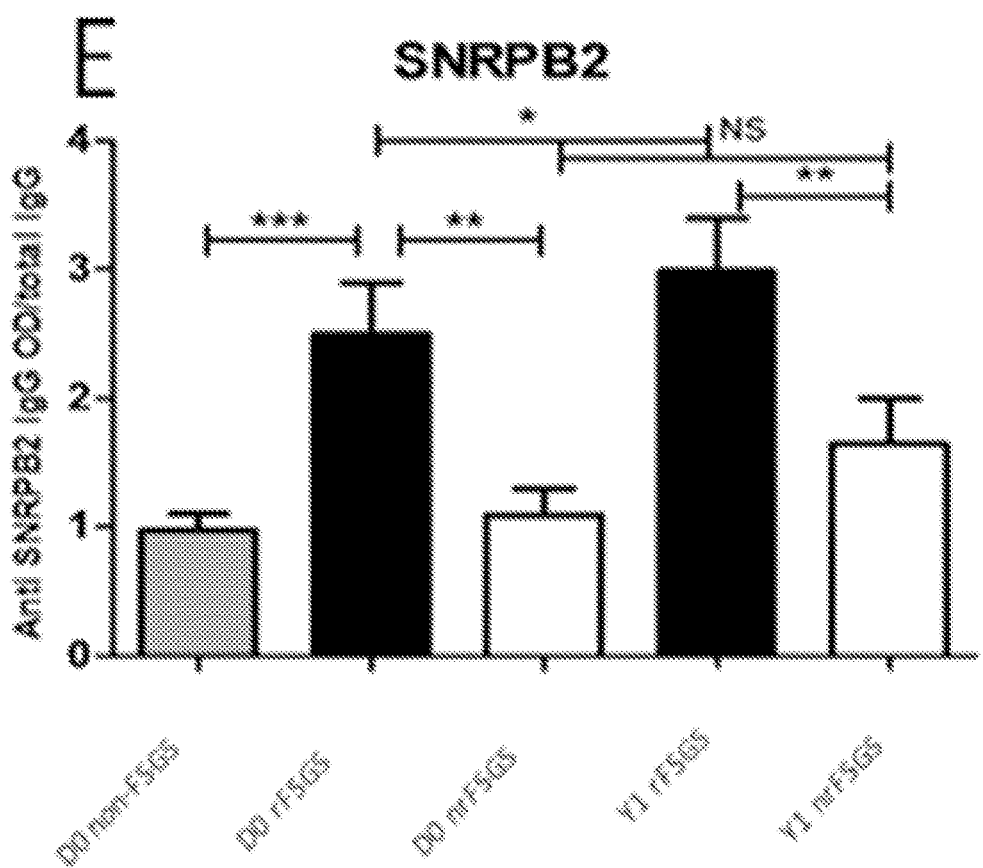
Figure 3:
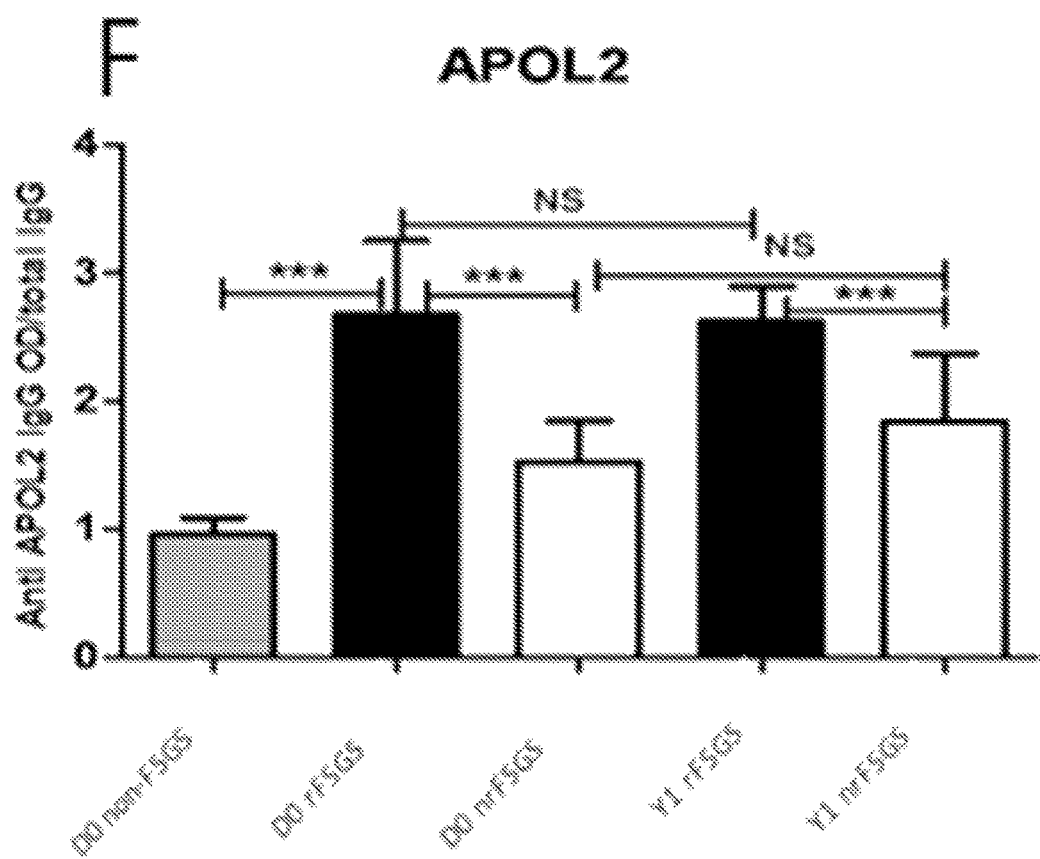
Figure 3:
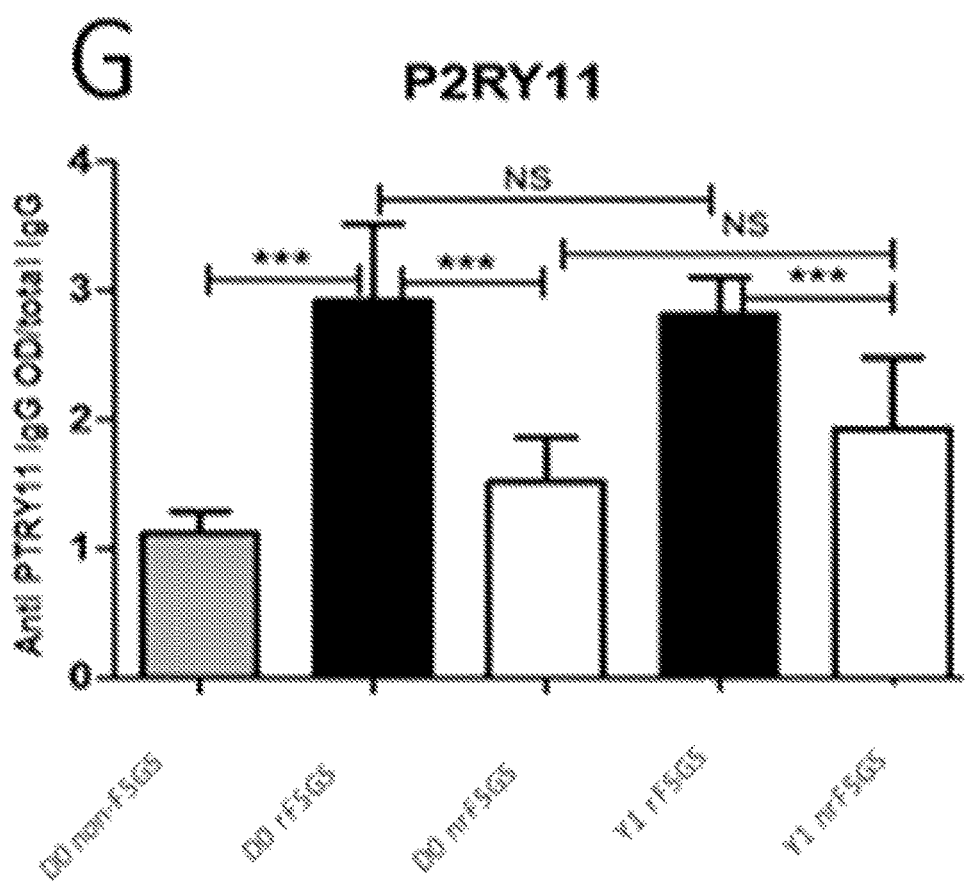
Figure 3:
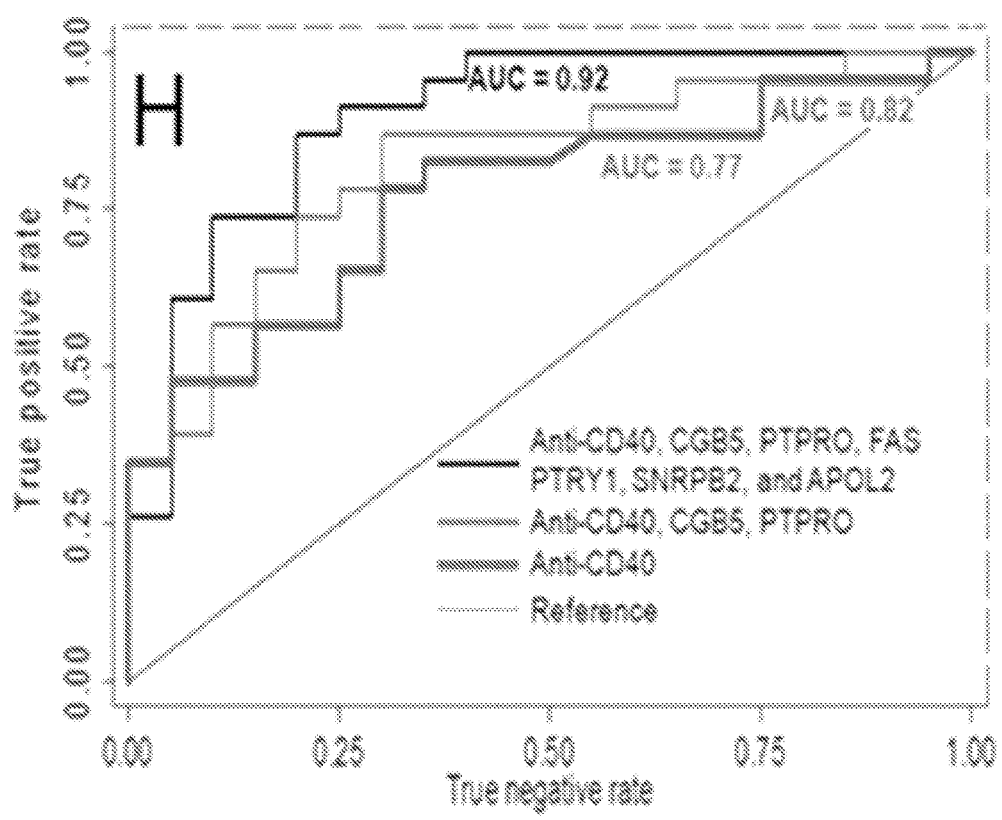

ELISA Validation of Antibodies that can Predict rFSGS after Renal Transplantation-Cross-Sectional and Longitudinal Analyses Customized ELISA assays were generated as previously described [18] for the autoantibodies shown in Table 2. 132 unique sera were processed for customized ELISA assays for all 10 autoantibodies in Table 2. Sera were obtained from 55 patients with FSGS as a cause of ESRD prior to transplantation; 27 of these patients had rFSGS within the first year post-transplant and 28 did not. Patients were demographically matched (Table 1) (FIG. 1). In a subset of these patients, follow-up sera samples were available at one year post-transplantation (17 with rFSGS in the first post-transplant year and 26 patients without recurrence); the customized ELISA assays for all 10 autoantibodies were also run on these samples to obtain a longitudinal analysis of antibody titres in the first post-transplant year. ELISA analyses confirmed that antibodies against CD40 (p=0.0002), SNRBP2 (p=0.0044), FAS (p=0.0035), PTPRO (p=0.015), P2RY11 (p=0.019), RXRA (p=0.01), CCL19 (p=0.015), MYLK (p=0.016), APOL2 (p=0.024) and CGB5 (p=0.031) and were all at statistically significant increased levels in sera samples from patients with post-transplant rFSGS, immediately before transplantation (Table 2, FIG. 3). This difference remained significant at one year post-transplantation for a subset of these antibodies against CGB5 (p=0.0001), FAS (p=0.0001), CD40 (p=0.0002), PTPRO (p=0.0005), APOL2 (p=0.0005), P2RY11 (p=0.0004) and SNRBP2 (p=0.035) (FIG. 3). In the longitudinal analysis, only anti-CD40 antibodies decreased between pre-transplantation and one year post-transplantation in rFSGS patients who had resolution of proteinuria secondary to Rituximab and intravenous cyclosporin A (5.3±1.2 vs 3.8±0.7 arbitrary units, p=0.087).

Receiver Operating Characteristic (ROC) analysis was conducted on the entire panel of autoantibody to find the best autoantibodys to predict rFSGS. For this purpose, we used three fitted logistic regression models using log-transformed ELISA levels of antibodies against CD40, FAS, PTPRO, P2RY11, CGB5, SNRBP2, and APOL2. This 7 antibody panel was able to predict rFSGS with an AUC of 0.90 (CI: 0.81-0.99). A second model included 3 antibodies (CD40, PTPRO, CGB5) and predicted rFSGS with an AUC of 0.82 (CI: 0.70-0.95). A third model with only anti-CD40 antibody predicted rFSGS with an AUC of 0.77 (CI:0.63-0.92)(FIG. 3).

Example 4

Characterizing CD40 Immune Reactive Epitopes in FSGS

Figure 4:
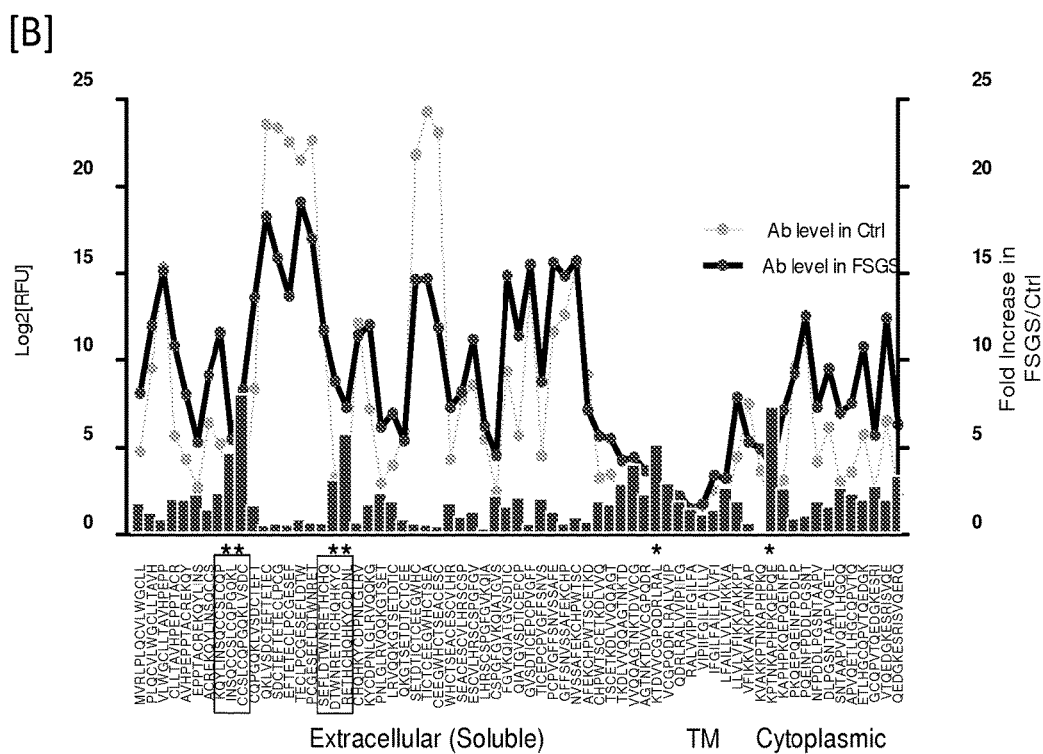
FIG. 4 shows the anti-CD40 antibody response towards different CD40 epitopes as assessed among FSGS and non-FSGS controls. Panel [A] shows increased antibody response against vicinity of two beta strand regions of CD 40 (NSQCC (SEQ ID NO: 1) and ESEF (SEQ ID NO: 2)) was observed. Panel [B] shows antibody levels against different epitopes (SEQ ID NO: 3-69, from left to right) spanning 15 AA across full-length CD40 protein was assessed using FSGS (n=4, black circles) and non-FSGS control (n=4, gray circles). Average fold increase in antibody response against different antigenic epitopes is presented as black bars. FSGS specific increase in terms of $p \leq 0.05$ and $\geq 2$ fold increase in FSGS are boxed.

Since CD40 autoantibody is an important factor in predicting rFSGS, further studies were carried out. It was hypothesized that there could be altered immune reactivity of the CD40 antigen in FSGS, to support the identification of increased levels of anti-CD40 antibodies in rFSGS. To test this hypothesis, 15 amino acid long synthetic peptides were custom synthesized to span the entire CD40 protein, using the PepStar™ Peptide Microarrays peptide array platform (JPT Technologies, Germany). This customized peptide array was hybridized with sera from 4 rFSGS patients and 4 non-FSGS control patients to measure the reactivity of different epitopes across CD40 antigen (FIG. 4) in these two different clinical patient groups. Sera from the rFSGS patients demonstrated significantly increased altered immunogenicity of the CD40 protein in the vicinity of two β-strand region (NSQCC) (SEQ ID NO: 1) and ESEF (SEQ ID NO: 2) as measured by increased antibody responses. This altered reactivity profile of the anti-CD40 IgG isolated from patients with rFSGS towards different epitopes of CD40 suggests that there is likely a perturbation in the conformation of either/and the CD40 protein and the anti-CD40 IgG antibody in rFSGS.

Example 5

CD40 is Expressed in Human Podocytes

Next, it was examined whether podocytes, as the primary target cell in FSGS express the CD40 protein. It was found that CD40 is expressed in both non-differentiated and differentiated cultured human podocytes. Incubating podocytes with either non-FSGS or non-recurrent FSGS or rFSGS patient sera did not distinguish podocyte CD40 expression. Similarly, LPS or TNFα did not alter podocyte CD40 either.

Example 6 rFSGS Derived CD40 Autoantibody Disrupts Podocyte Actin Cystoskeleton

Figure 5:
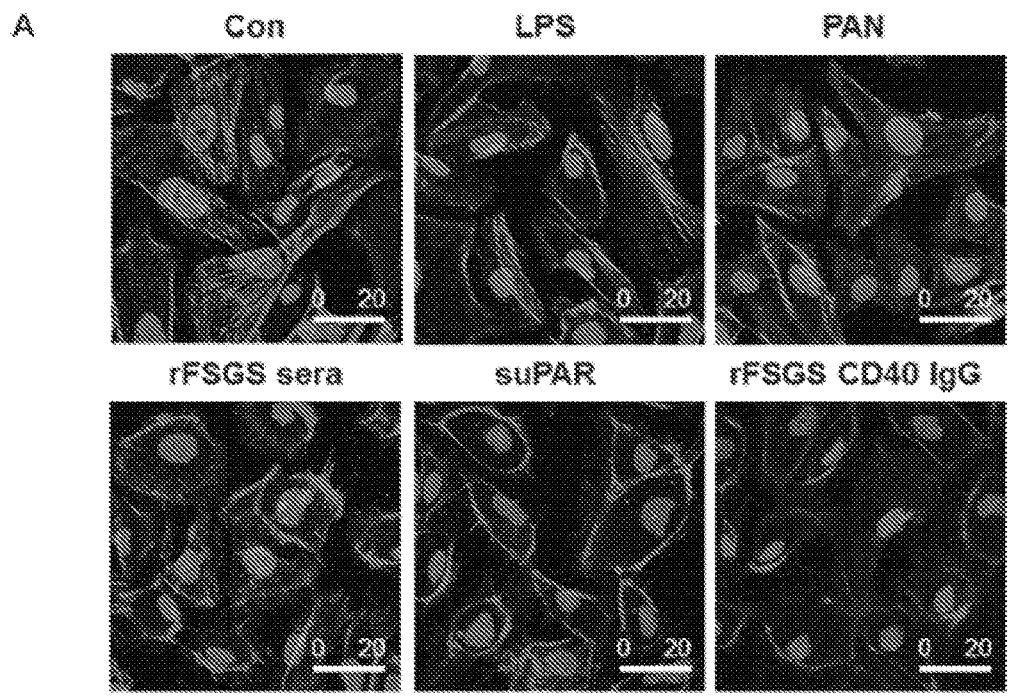
FIG. 5 shows that podocyte depolarization by CD40 autoantibody is preventable by CD40 blocking monoclonal antibody in rFSGS. Panel [A]: Completely differentiated human podocytes received the following treatments, and were stained with Phalloidin for F-actin analysis. Con: PBS control. LPS, 50 µg/ml. PAN 50 µg/ml. FSGS sera, 2% pretransplant sera from rFSGS patients, recombinant suPAR at 1 µg/ml. CD40 autoantibody from FSGS patients. Treatment of purified CD40 autoantibody and the FSGS sera which contains high level of CD40 autoantibodies depolarized podocytes with F-actin aggregated peripherally, and expression decreased centrally. Treatment of suPAR generated a similar phenotype, and that cotreatment of CD40 autoantibody together with suPAR monoclonal antibodies or cycloRGDfv, a small molecule blocking αvβ3 integrin activity mitigated the CD40 autoantibody induced podocyte depolarization. Panel [B]: Completely differentiated human podocytes were treated with a monoclonal CD40 antibody to examine its effect on CD40 autoantibody induced podocyte injury. Con, PBS control. CD40 autoantibody, D40 autoantibody purified from rFSGS patient sera, 2 µg/ml. CD40 Monoclonal Ab, a CD40 monoclonal antibody used at 1:1 ratio versus CD40 autoantibody. Note that cotreatment of CD40 blocking antibody together with CD40 autoantibody reduced the later induced F-actin alteration. Panel [C] shows that blocking suPAR-b3 integrin pathway ameliorates podocyte depolarization caused by human anti-CD40/rFSGS Ab. Completely differentiated human podocytes were cotreated with rFSGS CD40 IgG and suPAR-blocking monoclonal Ab (suPAR mAb, 1 mg/ml) or cycloRGDfV (1 mg/ml), a small molecule inhibiting aVb3 integrin activity. Compared to rFSGS CD40 IgG alone, cotreatment with suPAR-blocking monoclonal Ab or cycloRGDfV increased podocyte polarity (left panel) and F-actin levels (right panel). One-way analysis of variance (ANOVA) was used to calculate P values (provided in the figure), and a P value <0.05 was considered significant. Scale bars, 20 mm.
Figure 5:
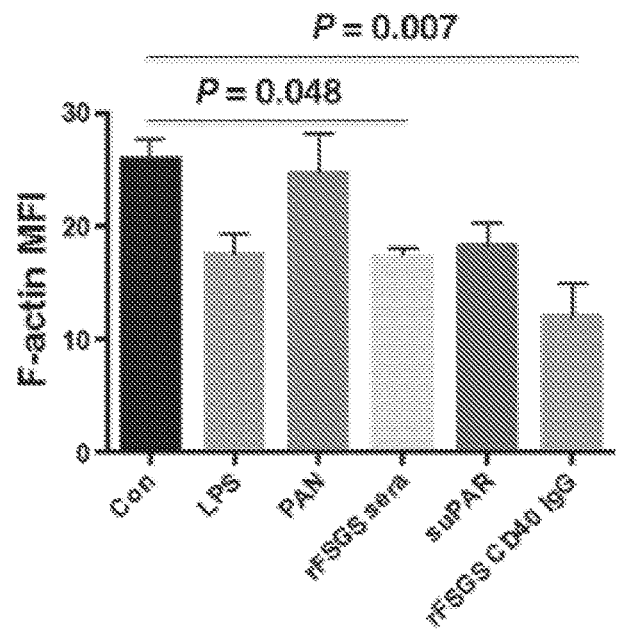
Figure 5:
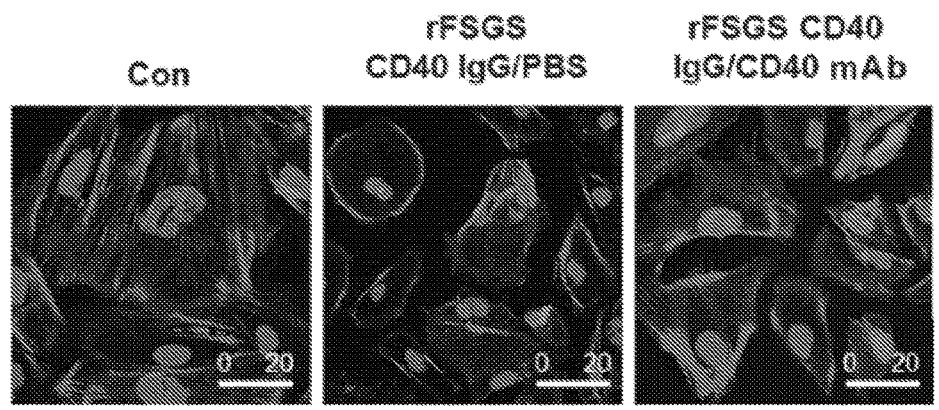
Figure 5:
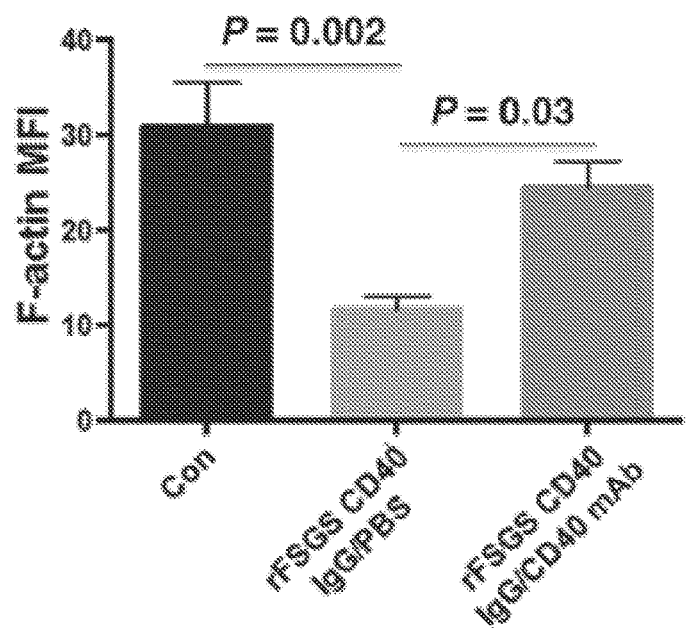
Figure 5:
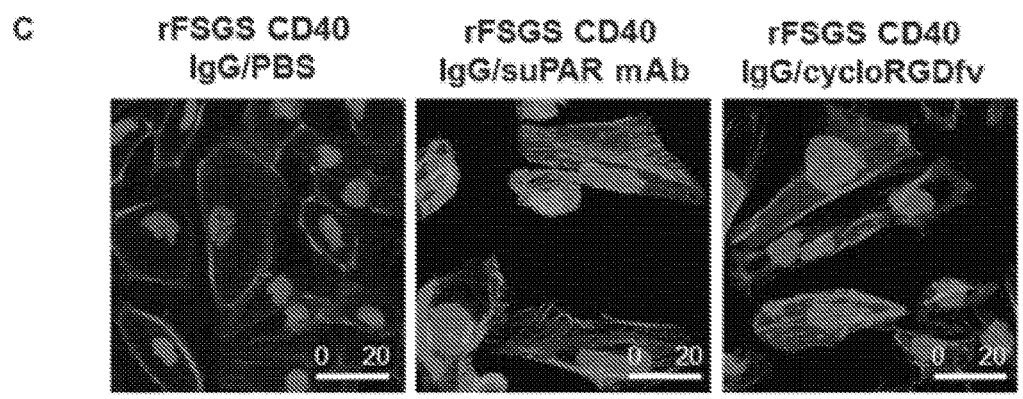
Figure 5:
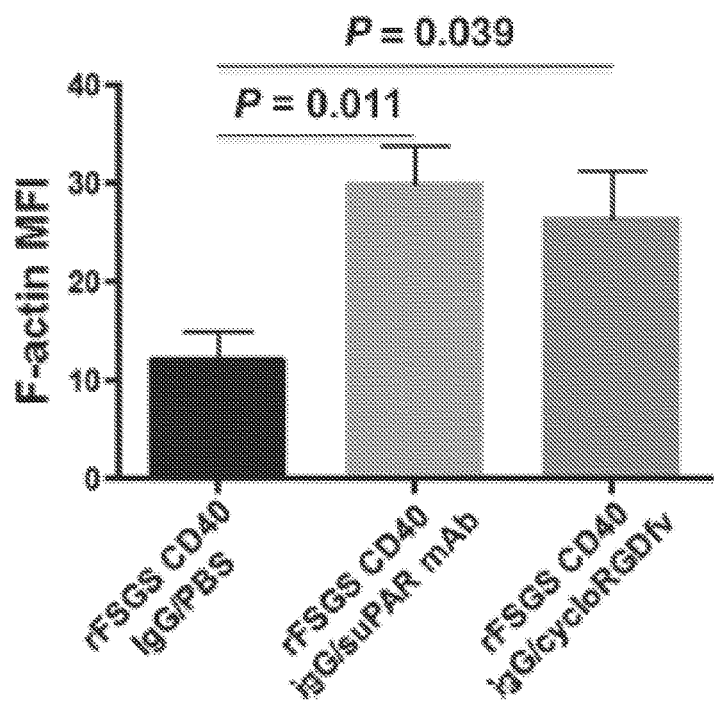

To examine the effect of CD40 autoantibody on podocyte biology, differentiated human podocytes were treated with either rFSGS sera or CD40 autoantibody purified from rFSGS patients, with LPS, PAN, suPAR as injury factor control. Compared to PBS control, it was found that rFSGS sera or CD40 autoantibodies caused podocyte depolarization and a reduction in overall cell size. Phalloidin staining shows that F-actin was diminished and reorganized peripherally, leading to a reduction in the total amount of cellular F-actin filament, especially in the center of the cells (FIG. 5A). Quantification analysis indicates that F-actin decreased significantly with podocytes treated with CD40 autoantibodies (FIG. 5A).

Considering the structure and/or spatial conformation of the CD40 autoantibody, it was explored whether blocking CD40 monoclonal antibody could interfere the CD40 autoantibody in CD40 binding. Thus cultured human podocytes were co-treated with both the CD40 autoantibody from rFSGS sera and a commercial monoclonal CD40 blocking antibody. It was found that co-treatment with blocking CD40 antibodies at 1:1 ratio prevented partially the autoantibody induced podocyte depolarization (FIG. 5B). These results suggest that the CD40 blocking antibody could compete with the purified CD40 autoantibody for CD40 binding, and could help correct the CD40 autoantibody derived podocyte injury.

Since the suPAR, a recently identified FSGS factor, elicited a similar response on podocyte F-actin filaments (FIG. 5A) as did the CD40 autoantibody, it was investigated if the suPAR-beta3 integrin signaling pathway might play a role in the CD40 autoantibody induced podocyte damage. Indeed, co-treatment of podocytes with both CD40 autoantibodies and monoclonal SuPAR blocking antibodies resulted in an ameliorated podocyte injury response and less podocyte actin depolarization. This phenomenon was also observed in the podocytes treated with both, CD40 autoantibody and cycloRGDfv, a small molecule that blocksalphaVbeta3 integrin activity. While further studies are necessary deciphering the detailed mechanisms of the combined CD40-suPAR cascade, these results put together suggest that suPAR-beta3 integrin signalling is involved in the CD40 autoantibody-induced podocyte injury as well.

FIG. 5C shows that blocking suPAR-b3 integrin pathway ameliorates podocyte depolarization caused by human anti-CD40/rFSGS Ab. Completely differentiated human podocytes were cotreated with rFSGS CD40 IgG and suPAR-blocking monoclonal Ab (suPAR mAb, 1 mg/ml) or cycloRGDfV (1 mg/ml), a small molecule inhibiting aVb3 integrin activity. Compared to rFSGS CD40 IgG alone, cotreatment with suPAR-blocking monoclonal Ab or cyclo-RGDfV increased podocyte polarity (left panel) and F-actin levels (right panel). One-way analysis of variance (ANOVA) was used to calculate P values (provided in the figure), and a P value <0.05 was considered significant. Scale bars, 20 mm.

Example 7 rFSGS Derived CD40 Autoantibody Induced Albuminuria in Mice

Figure 6:
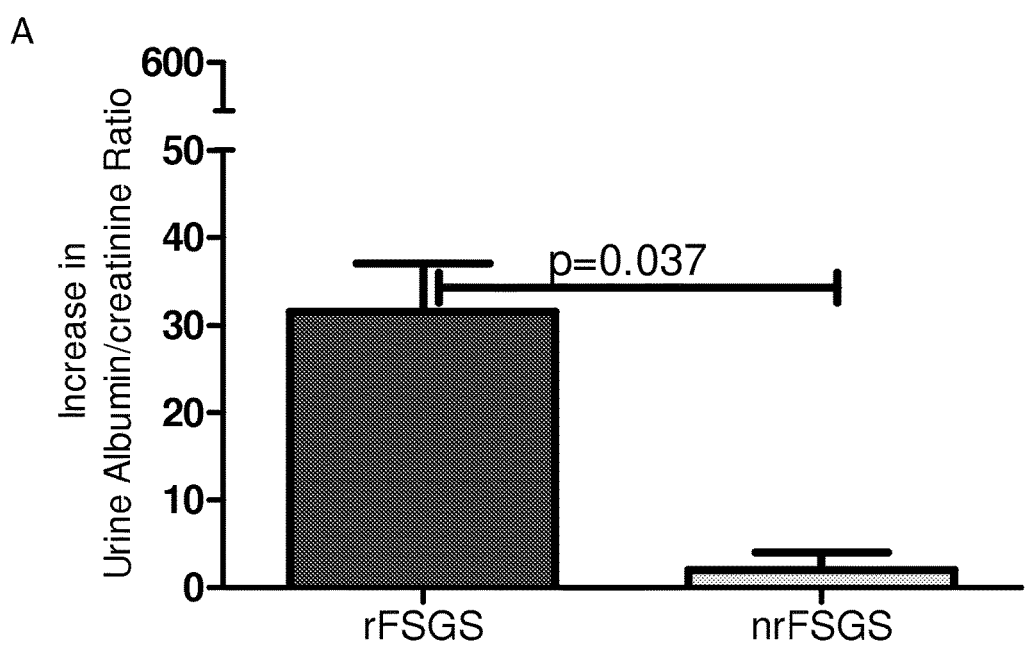
FIG. 6 shows the induction of proteinuria by anti-CD40 IgG, suPAR and the role of mouse monoclonal anti-CD40. Panel [A]: Increase in proteinuria caused in mice due to injection of anti-CD40 antibody isolated from rFSGS and nrFSGS patients; Panel [B]: Significant increase in proteinuria caused in mice due to injection of anti-CD40 isolated from rFSGS patients in combination with suPAR compared to anti-CD40 isolated from rFSGS patients in combination with suPAR; Panel [C]: Reduction of proteinuria caused by anti-CD40 antibody and suPAR in mice when mouse anti-human CD40 monoclonal antibody was supplemented after induction of proteinuria.
Figure 6:
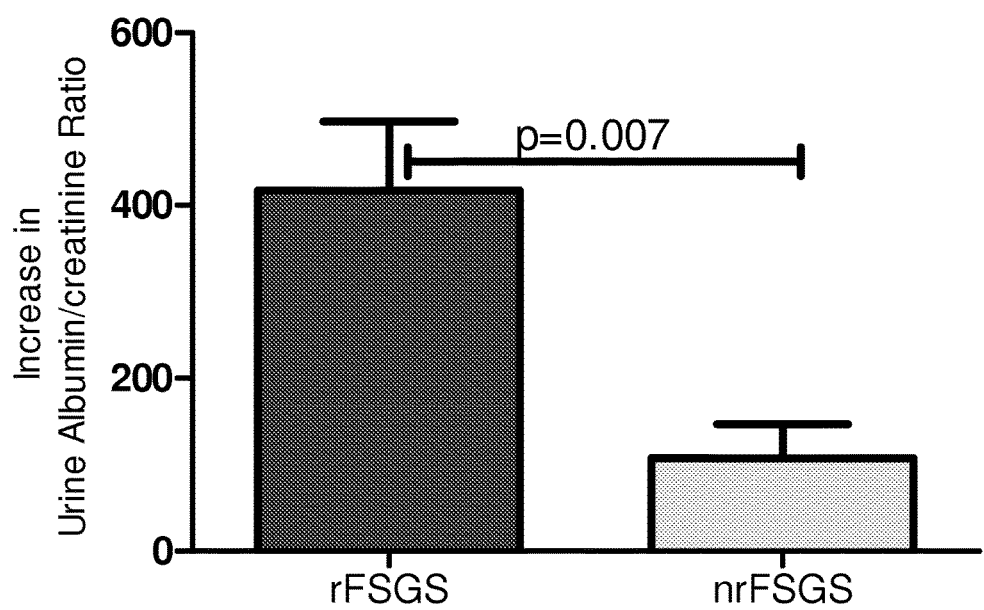
Figure 6:
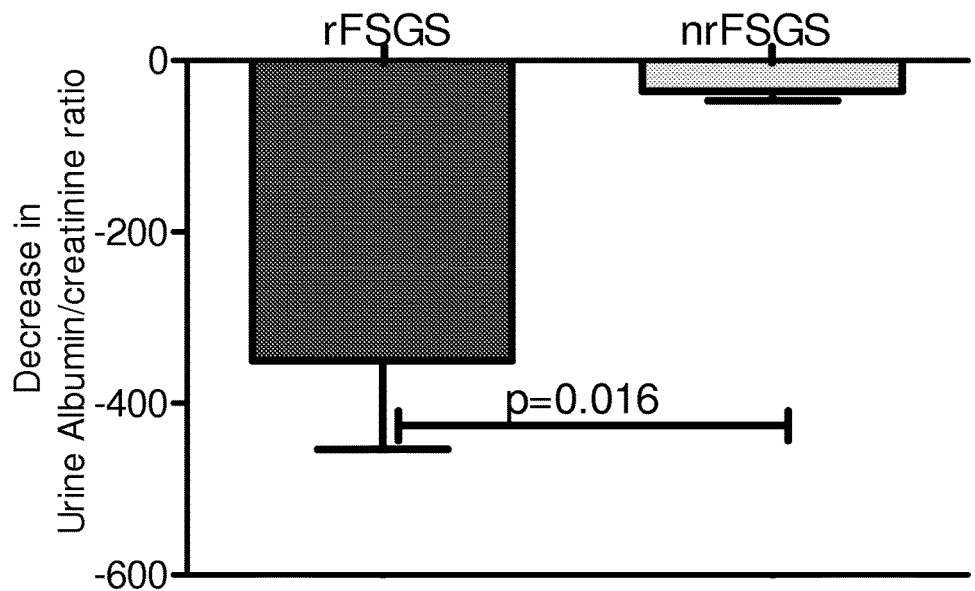

Next, it was tested whether CD40 autoantibody could induce a renal injury phenotype in terms of proteinuria. First, CD40 autoantibodies isolated from sera of patients with and without rFSGS, was injected into B6 mice (n=5 in each group). Urine albumin to ceatinine ratio (UACR) was calculated on days 1-8, with the CD40 autoantibody injection occurring on Days 1 and 3. A significant increase in proteinuria on day 8 compared to day 0 was observed (delta increase of UACR of 31±7.8 with rFSGS CD40 antibody vs 4±2.8 with nrFSGS CD40 Ab) (FIG. 6A). When, in a separate experiment, concurrent single injection of suPAR recombinant protein to CD40 autoantibody-receiving mice 6 hr after the $6^{th}$ dose of anti-CD40 antibody significantly enhanced proteinuria. The increase in proteinuria caused by anti-CD40 autoantibodies isolated from rFSGS patients with suPAR was significantly higher (417.2±8) compared to increase in proteinuria caused by anti-CD40 autoantibodies isolated from nrFSGS patients (107.7±39.0) a p value 0.007 (FIG. 6B). Administration of a blocking antibody (mouse monoclonal blocking antibody to CD40) quickly abolished proteinuria, which however bounced back a few days later. The degree of decrease in proteinuria after the administration of the blocking antibody was greater with the mice administered with anti-CD40 autoantibodies from rFSGS (350.1±103.2) when compared to the decrease in proteinuria in the mice administered with anti-CD40 antibody from nrFSGS (36.1±11.0) with a p value 0.016 (FIG. 6C).

Figure 7:
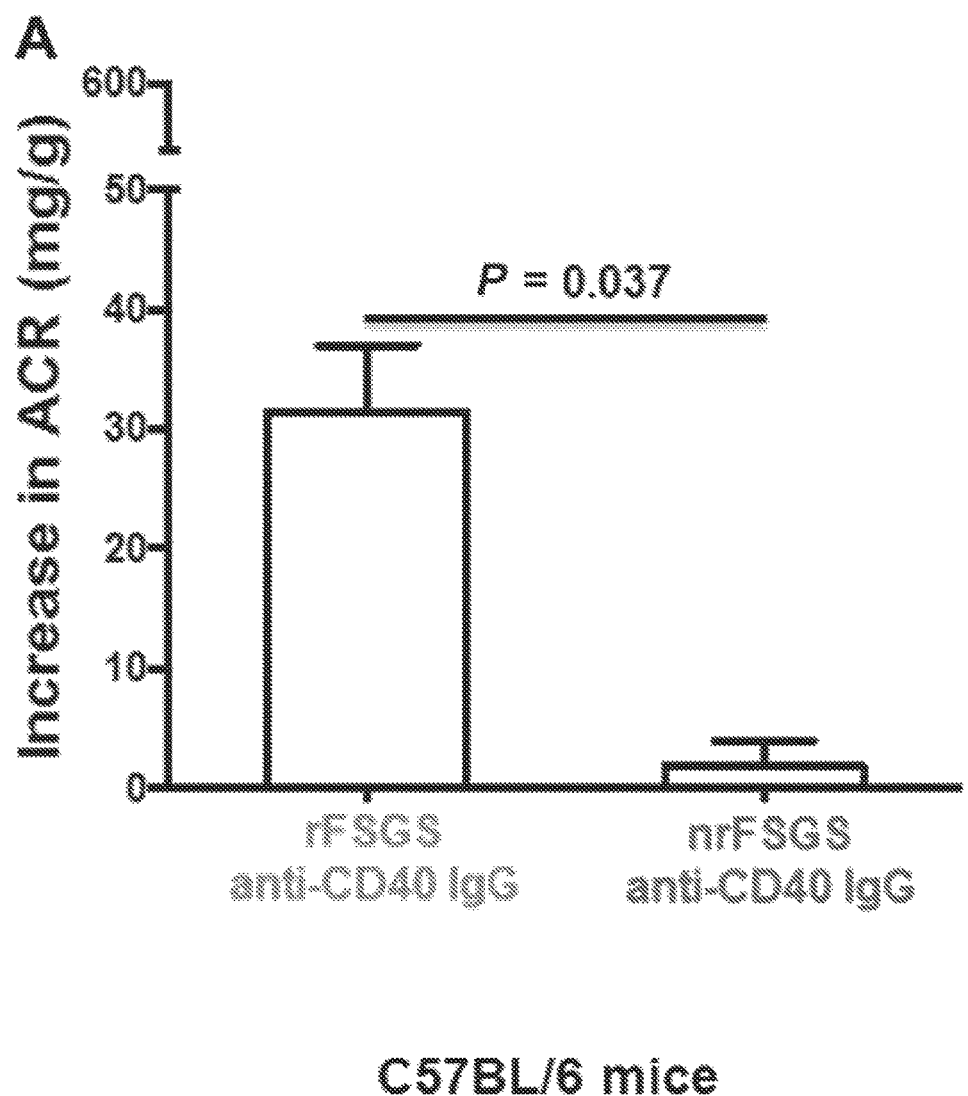
FIG. 7. shows the induction of proteinuria with human anti-CD40 Ab/rFSGS in mice. (Panels A to E) Wild-type C57BL/6 mice (A to C) or CD40−/− mice (Panels D and E) were treated with anti-CD40 Ab isolated from rFSGS or nrFSGS patients. The change in ACR was greater when C57BL/6 mice were injected with two doses of anti-CD40 Ab/rFSGS compared to anti-CD40 Ab/nrFSGS; the change in ACR between day 0 and day 8 is shown in (Panel A). With co-injection of suPAR, the increase in ACR was again greater in C57BL/6 mice injected with anti-CD40 Ab/rFSGS, and proteinuria increased more than threefold from a baseline of 102.9±7 (Panel B). Injection of CD40-blocking Ab into C57BL/6 mice cotreated with suPAR and anti-CD40 Ab/rFSGS significantly reduced proteinuria (Panel C). Injection of anti-CD40 Ab/rFSGS into CD40−/− mice did not cause significant proteinuria (Panel D). CD40−/− mice cotreated with anti-CD40 Ab/rFSGS and suPAR showed a significant increase in ACR, but this was not seen when these mice were cotreated with anti-CD40 Ab/nrFSGS and suPAR (Panel E). P values (provided in the figure) were determined with unpaired t test calculated in GraphPad Prism. A P value of <0.05 was considered significant.
Figure 7:
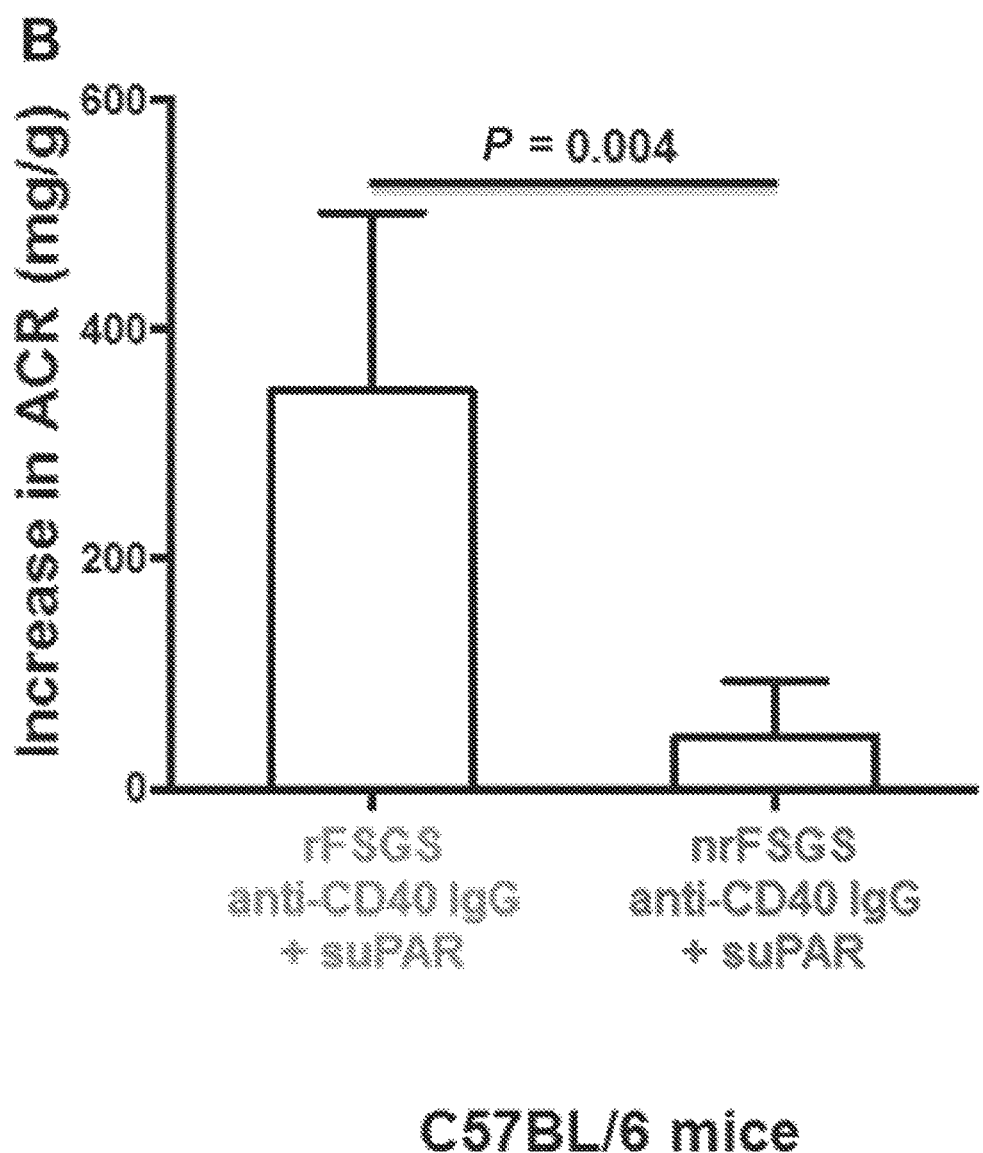
Figure 7:
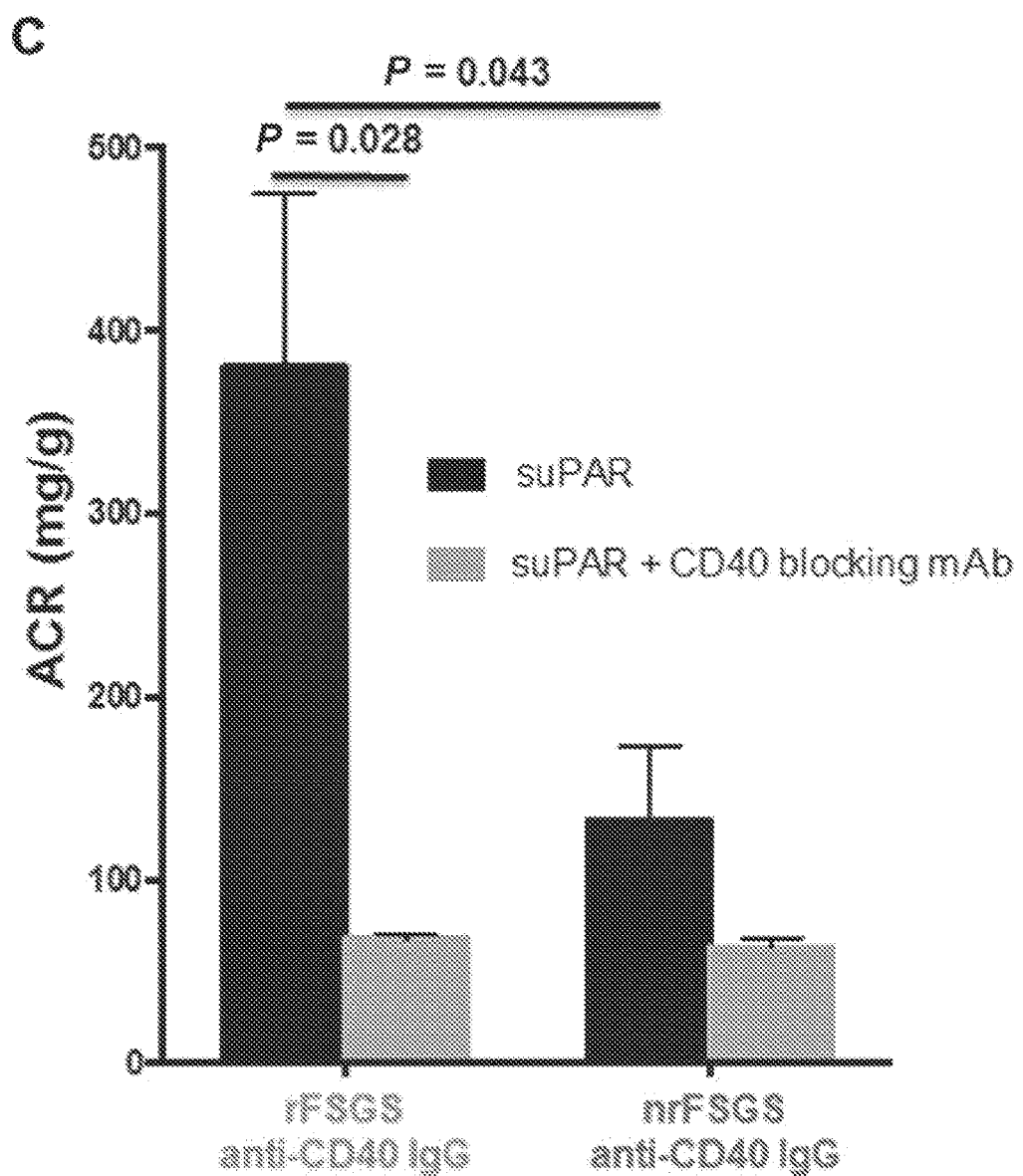
Figure 7:
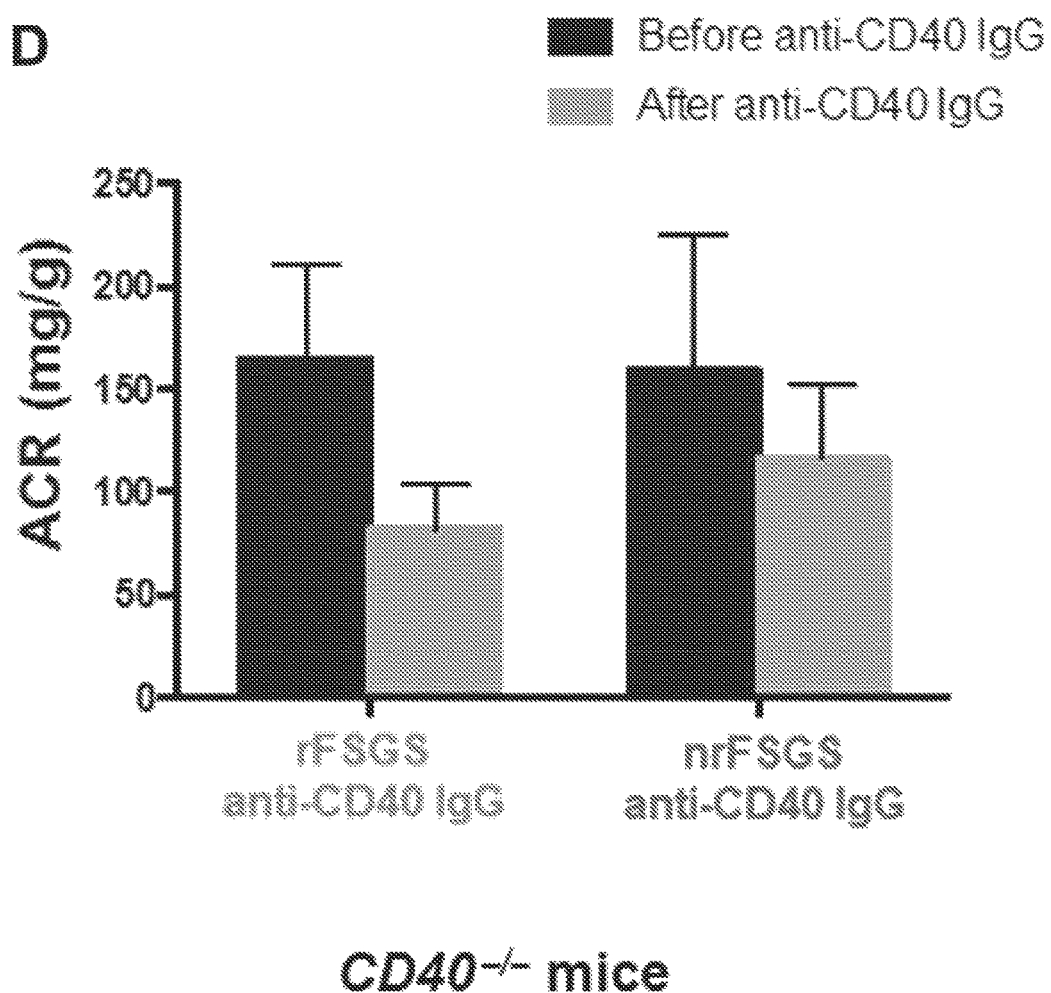
Figure 7:
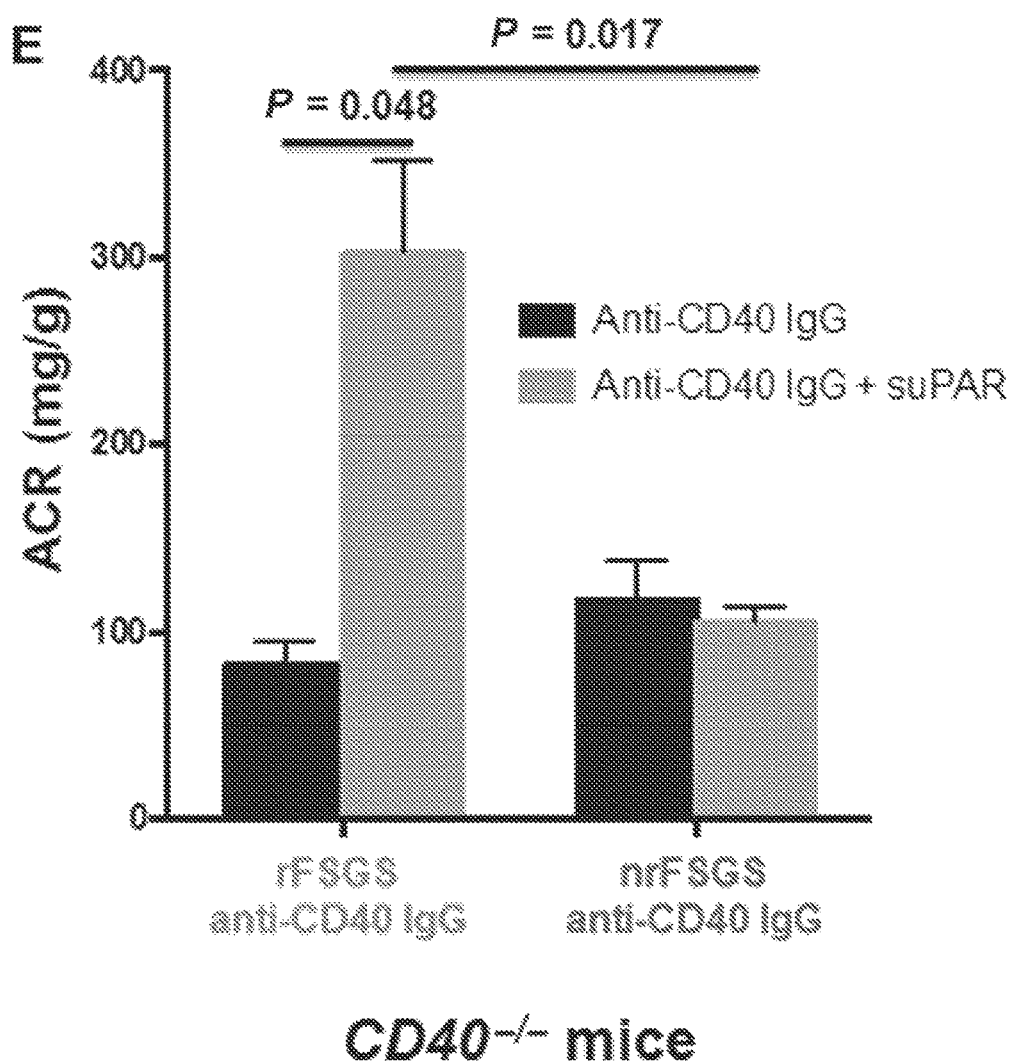

FIG. 7. shows the induction of proteinuria with human anti-CD40 Ab/rFSGS in mice. (FIG. 7A to E) Wild-type C57BL/6 mice (A to C) or CD40−/− mice (FIGS. 7D and E) were treated with anti-CD40 Ab isolated from rFSGS or nrFSGS patients. The change in ACR was greater when C57BL/6 mice were injected with two doses of anti-CD40 Ab/rFSGS compared to anti-CD40 Ab/nrFSGS; the change in ACR between day 0 and day 8 is shown in (FIG. 7A). With co-injection of suPAR, the increase in ACR was again greater in C57BL/6 mice injected with anti-CD40 Ab/rF-SGS, and proteinuria increased more than threefold from a baseline of 102.9±7 (FIG. 7B). Injection of CD40-blocking Ab into C57BL/6 mice cotreated with suPAR and anti-CD40 Ab/rFSGS significantly reduced proteinuria (FIG. 7C). Injection of anti-CD40 Ab/rFSGS into CD40−/− mice did not cause significant proteinuria (FIG. 7D). CD40−/− mice cotreated with anti-CD40 Ab/rFSGS and suPAR showed a significant increase in ACR, but this was not seen when these mice were cotreated with anti-CD40 Ab/nrFSGS and suPAR (FIG. 7E). P values (provided in the figure) were determined with unpaired t test calculated in GraphPad Prism. A P value of <0.05 was considered significant.

Figure 8:
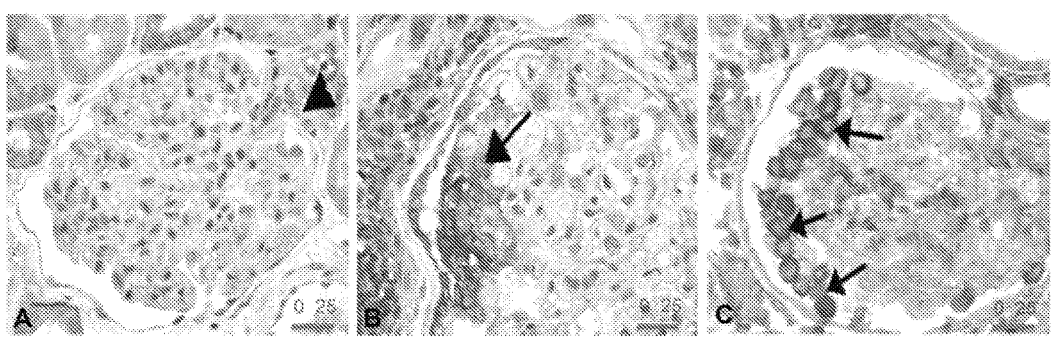
FIG. 8 shows IHC of CD40 staining in kidney biopsies from patients with rFSGS. (Panel A) No CD40 staining is observed in the podocytes of this normal human glomerulus from the tumor-free part of a total nephrectomy for renal cell carcinoma. Vascular hilum is marked by an arrowhead. (Panel B) Focal podocyte labeling for CD40 (arrow) in a case of rFSGS. (Panel C) Strong CD40 signal is observed in the hyperplastic podocytes (arrows) covering an rFSGS lesion. Scale bars, 25 mm.

FIG. 8 shows IHC of CD40 staining in kidney biopsies from patients with rFSGS. (FIG. 8A) No CD40 staining is observed in the podocytes of this normal human glomerulus from the tumor-free part of a total nephrectomy for renal cell carcinoma. Vascular hilum is marked by an arrowhead. (FIG. 8B) Focal podocyte labeling for CD40 (arrow) in a case of rFSGS. (FIG. 8C) Strong CD40 signal is observed in the hyperplastic podocytes (arrows) covering an rFSGS lesion. Scale bars, 25 mm.

TABLE 1

Demographics of Patients with the non-recurrent (nrFSGS) and recurrent FSGS (rFSGS) subdivided into the Test-Set (Protoarray Discovery) and the Validation-Set (ELISA Validation)

| | Test set | | | Validation set | | |
| --- | --- | --- | --- | --- | --- | --- |
| Parameters | nrFSGS (N = 10) | FSGS (N = 10) | p-value | nrFSGS (N = 21) | FSGS (N = 18) | p-value |
| Age nephrotic syndrom begin (year, mean ± SE) | 23.4 ± 2.9 | 28.2 ± 4.8 | 0.77 | 26.6 ± 3.4 | 23.2 ± 2.8 | 0.57 |
| Race (% Black) | 30% | 50% | 0.65 | 29% | 38% | 0.51 |
| Sex (% Male) | 80% | 60% | 0.63 | 85% | 61% | 1.00 |
| Steroids on native kidney (% yes) | 70% | 50% | 0.65 | 73% | 72% | 1.00 |
| Cyclosporine on native kidney (% yes) | 30% | 30% | 1.00 | 53% | 61% | 0.73 |

TABLE 1-continued

Demographics of Patients with the non-recurrent (nrFSGS) and recurrent FSGS (rFSGS) subdivided into the Test-Set (Protoarray Discovery) and the Validation-Set (ELISA Validation)

| Parameters | Test set | | | Validation set | | |
|---|---|---|---|---|---|---|
| | nrFSGS (N = 10) | FSGS (N = 10) | p-value | nrFSGS (N = 21) | FSGS (N = 18) | p-value |
| Nephrotic syndrom native kidney (% yes) | 50% | 80% | 0.34 | 62% | 77% | 0.32 |
| Previous transplantation (% yes) | 30% | 10% | 0.58 | 33% | 44% | 0.52 |
| Year to ESRD (year, mean ± SE) | 5.4 ± 1.0 | 5.9 ± 2.0 | 0.70 | 6.7 ± 1.9 | 7.1 ± 1.7 | 0.69 |
| Cumulative time on dialysis (year, mean ± SE) | 4.9 ± 1.1 | 3.3 ± 1.0 | 0.19 | 5.2 ± 0.9 | 3.5 ± 0.7 | 0.21 |
| Weight Day 0 (kg, mean ± SE) | 76.7 ± 9.5 | 69.5 ± 2.4 | 0.76 | 68 ± 3 | 76 ± 5 | 0.33 |
| Gamma globulin Day 0 (g/l, mean ± SE) | 11.0 ± 1.2 | 12.8 ± 1.4 | 0.23 | 9.7 ± 1.2 | 12.8 ± 1.4 | 0.13 |
| Delayed graft function (% yes) | 10% | 40% | 0.30 | 19% | 16% | 1.00 |
| Number of dialysis post-Tx (N, mean ± SE) | 0.4 ± 0.4 | 1.2 ± 0.8 | 0.18 | 0.7 ± 0.4 | 0.5 ± 0.3 | 0.64 |
| Rejection (% yes) | 20% | 10% | 1.00 | 33% | 33% | 1.00 |
| Sepsis (% yes) | 40% | 40% | 1.00 | 14% | 11% | 1.00 |
| CRP (during the first 10 days post-Tx) (mg/L, mean ± SE) | 36 ± 13 | 39 ± 15 | 0.73 | 21.6 ± 4.6 | 24.1 ± 7.7 | 0.93 |
| Serum creat at 3 months (mmol/l, mean ± SE) | 122 ± 9 | 145 ± 30 | 0.08 | 157 ± 14 | 130 ± 10 | 0.18 |
| Serum creatinin at Last Follow up (mmol/l, mean ± SE) | 146 ± 26 | 205 ± 38 | 0.27 | 158 ± 15 | 172 ± 26 | 0.97 |

TABLE 2

10 Autoantibody Significantly Elevated in Sera of Patients with rFSGS

| Protein targets for the 10 most Significant Auto-Ab Elevated in Sera of Patients with rFSGS | Gene Symbol | Significance Levels by ProtoArray Discovery (pre-transplant sera; rFSGS vs nrFSGS, p value) | Significance Levels by ELISA Validation (pre-transplant sera; rFSGS vs FSGS and non-nrFSGS controls, p value) |
|---|---|---|---|
| CD40 molecule-TNF receptor superfamily member 5 | CD40 | 0.0027 | 0.0002 |
| TNF receptor superfamily member 6 | FAS | 0.0015 | 0.0035 |
| chemokine (C-C motif) ligand 19 | CCL19 | 0.028 | 0.015 |
| myosin light kinase | MYLK | 0.034 | 0.016 |
| chorionic gonadotropin beta | CGB5 | 0.00035 | 0.031 |
| ribonucleoproteinB small nuclear | SNRBP2 | 0.00035 | 0.0044 |
| retinoid X receptor, alpha | RXRA | 0.0098 | 0.01 |
| P2Y purinoceptor 11 | P2RY11 | 0.0054 | 0.019 |
| protein tyrosine phosphatase, receptor O | PTPRO | 0.043 | 0.015 |
| Apolipoprotein 2 | APOL2 | 0.043 | 0.024 |

REFERENCES

1. D'Agati, V. D., F. J. Kaskel, and R. J. Falk, *Focal segmental glomerulosclerosis.* N Engl J Med, 2011. 365(25): p. 2398-411.
2. Gbadegesin, R., et al., *Pathogenesis and therapy of focal segmental glomerulosclerosis: an update.* Pediatr Nephrol, 2010.
3. Canaud, G., et al., *Recurrence of nephrotic syndrome after transplantation in a mixed population of children and adults: course of glomerular lesions and value of the Columbia classification of histological variants of focal and segmental glomerulosclerosis (FSGS).* Nephrol Dial Transplant, 2010. 25(4): p. 1321-8.
4. Pardon, A., et al., *Risk factors and outcome of focal and segmental glomerulosclerosis recurrence in adult renal transplant recipients.* Nephrol Dial Transplant, 2006. 21(4): p. 1053-9.
5. Vinai, M., P. Waber, and M. G. Seikaly, *Recurrence of focal segmental glomerulosclerosis in renal allograft: an in-depth review.* Pediatr Transplant, 2010. 14(3): p. 314-25.
6. Senggutuvan, P., et al., *Recurrence of focal segmental glomerulosclerosis in transplanted kidneys: analysis of incidence and risk factors in 59 allografts.* Pediatr Nephrol, 1990. 4(1): p. 21-8.
7. Wei, C., et al., *Circulating urokinase receptor as a cause of focal segmental glomerulosclerosis.* Nat Med, 2011. 17(8): p. 952-60.
8. Wei, C., et al., *Circulating suPAR in Two Cohorts of Primary FSGS.* J Am Soc Nephrol, 2012.
9. Pescovitz, M. D., B. K. Book, and R. A. Sidner, *Resolution of recurrent focal segmental glomerulosclerosis proteinuria after rituximab treatment.* N Engl J Med, 2006. 354(18): p. 1961-3.
10. Dantal, J., et al., *Antihuman immunoglobulin affinity immunoadsorption strongly decreases proteinuria in patients with relapsing nephrotic syndrome.* J Am Soc Nephrol, 1998. 9(9): p. 1709-15.
11. Musante, L., et al., *Circulating anti-actin and anti-ATP synthase antibodies identify a sub-set of patients with idiopathic nephrotic syndrome.* Clin Exp Immunol, 2005. 141(3): p. 491-9.
12. Charba, D. S., et al., *Antibodies to protein tyrosine phosphatase receptor type O (PTPro)increase glomerular albumin permeability (P(alb)).* Am J Physiol Renal Physiol, 2009. 297 (1): p. F138-44.
13. Topham, P. S., et al., *Nephritogenic mAb 5-1-6 is directed at the extracellular domain of rat nephrin.* J Clin Invest, 1999. 104 (11): p. 1559-66.
14. Savin, V. J., et al., *Circulating factor associated with increased glomerular permeability to albumin in recurrent focal segmental glomerulosclerosis.* N Engl J Med, 1996. 334 (14): p. 878-83.
15. Fornoni, A., et al., *Rituximab targets podocytes in recurrent focal segmental glomerulosclerosis.* Science translational medicine, 2011. 3 (85): p. 85ra46.
16. Chikamoto, H., et al., *Pretransplantation combined therapy with plasmapheresis and rituximab in a second* living-related kidney transplant pediatric recipient with a very high risk for focal segmental glomerulosclerosis recurrence. Pediatric transplantation, 2011.
17. Assmann, K. J., et al., *Antibody-induced albuminuria and accelerated focal glomerulosclerosis in the Thy-1.1 transgenic mouse.* Kidney Int, 2002. 62 (1): p. 116-26.
18. Sigdel, T. K., et al., *Non-HLA Antibodies to Immunogenic Epitopes Predict the Evolution of Chronic Renal Allograft Injury.* J Am Soc Nephrol, 2012.
19. Li, L., et al., *Identifying compartment-specific non-HLA targets after renal transplantation by integrating transcriptome and "antibodyome" measures.* Proc Natl Acad Sci USA, 2009. 106 (11): p. 4148-53.
20. Butte, A., et al., *Protein Microarrays Discover Angiotensinogen and PRKRIP1 as Novel Targets for Autoantibodies in Chronic Renal Disease.* Molecular & Cellular Proteomics, 2010 ((In Press)).
21. Sutherland, S. M., et al., *Protein microarrays identify antibodies to protein kinase Czeta that are associated with a greater risk of allograft loss in pediatric renal transplant recipients.* Kidney Int, 2009. 76 (12): p. 1277-83.
22. Peppard, J. V. and E. Orlans, *The biological half-lives of four rat immunoglobulin isotypes.* Immunology, 1980. 40 (4): p. 683-6.
23. Huang, J., et al., *Plasma soluble urokinase receptor levels are increased but do not distinguish primary from secondary focal segmental glomerulosclerosis.* Kidney Int, 2013. 84 (2): p. 366-72.
24. Alachkar, N., et al., *Podocyte effacement closely links to suPAR levels at time of posttransplantation focal segmental glomerulosclerosis occurrence and improves with therapy.* Transplantation, 2013. 96 (7): p. 649-56.
25. Trachtman, H., C. Wei, and J. Reiser, *Circulating factor in FSGS: a black sheep in the suPAR family?* Pediatr Nephrol, 2013. 28 (7): p. 1151-2.
26. Yu, H., et al., *Rac1 activation in podocytes induces rapid foot process effacement and proteinuria.* Mol Cell Biol, 2013. 33 (23): p. 4755-64.
27. Wei, C., et al., *Modification of kidney barrier function by the urokinase receptor.* Nat Med, 2008. 14 (1): p. 55-63.
28. Veron, D., et al., *Acute podocyte vascular endothelial growth factor (VEGF-A) knockdown disrupts alphaV-beta3 integrin signaling in the glomerulus.* PLoS One, 2012. 7 (7): p. e40589.
29. Bitzan, M., et al., *TNFalpha pathway blockade ameliorates toxic effects of FSGS plasma on podocyte cytoskeleton and beta3 integrin activation.* Pediatr Nephrol, 2012. 27 (12): p. 2217-26.
30. Le Berre, L., et al., *Renal macrophage activation and Th2 polarization precedes the development of nephrotic syndrome in Buffalo/Mna rats.* Kidney Int, 2005. 68 (5): p. 2079-90.
31. Grimbert, P., et al., *Truncation of C-mip (Tc-mip), a new proximal signaling protein, induces c-maf Th2transcription factor and cytoskeleton reorganization.* The Journal of experimental medicine, 2003. 198 (5): p. 797-807.
32. van Kooten, C., et al., *B cells regulate expression of CD40 ligand on activated T cells by lowering the mRNA level and through the release of soluble CD40.* Eur J Immunol, 1994. 24 (4): p. 787-92.
33. Tanaka T, et al., *Human platelets stimulate mesangial cells to produce monocyte chemoattractant protein-1 via the CD40/CD40 ligand pathway and may amplify glomerular injury.* J Am Soc Nephrol., 2002. 13 (10): p. 2488-96.
34. Kairaitis, L., et al., *Blockade of CD40-CD40 ligand protects against renal injury in chronic proteinuric renal disease.* Kidney Int, 2003. 64 (4): p. 1265-72.
35. Law, C. L. and I. S. Grewal, Therapeutic interventions targeting CD40L (CD154) and CD40: the opportunities and challenges. Adv Exp Med Biol, 2009. 647: p. 8-36.
36. Higgins, J. P., et al., Gene expression in the normal adult human kidney assessed by complementary DNA microarray. Mol Biol Cell, 2004. 15 (2): p. 649-56.

I claim:

1. A method of treating an individual who suffers from recurrent focal segmental glomerulosclerosis (rFSGS), native FSGS, minimal change disease, glomerular nephritis, membrano-proliferative glomerular nephritis (membranous), or IgA glomerular nephritis (membranous) comprising: a) contacting a biological sample from the individual with a binding agent for an autoantibody, wherein the autoantibody recognizes an antigen selected from the group consisting of CD40, PTPRO, CGB5, FAS, P2RY11, SNRPB2, APOL2, CCL 19, MYLK, and RXRA;
   b) detecting the binding of the binding agent to at least one autoantibody in the sample; and
   identifying the individual suffers at least one of the diseases above;
   (c) administering to the individual a blocking antibody that binds to a target selected from the group consisting of CD40, PTPRO, CGB5, FAS, P2RY11, SNRPB2, APOL2, CCL19, MYLK, and RXRA.

2. The method of claim 1 wherein the target is CD40 or PTPRO.

3. The method of claim 1 further comprising treating the individual with plasmapheresis.

4. The method of claim 1, wherein the antigen is CD40.

5. The method of claim 4, wherein the detecting the binding of the binding agent to at least one autoantibody in the sample comprises binding of the autoantibody to an epitope of the antigen comprising the amino acid sequence(s) NSQCC (SEQ ID No. 1) and/or ESEF (SEQ ID No. 2).

* * * * *